US012115261B2

(12) United States Patent
Kim et al.

(10) Patent No.: US 12,115,261 B2
(45) Date of Patent: Oct. 15, 2024

(54) BLOCK COPOLYMER COMPRISING HYDROPHILIC FIRST BLOCK, HYDROPHOBIC SECOND BLOCK, AND FUNCTIONAL GROUP CAPABLE OF SPECIFICALLY BINDING TO THIOL

(71) Applicant: GI CELL, INC., Seongnam-si (KR)

(72) Inventors: Won Jong Kim, Pohang-si (KR); Dong Hyun Jang, Yongin-si (KR)

(73) Assignee: GI CELL, INC., Gyeonggi-do (KR)

( * ) Notice: Subject to any disclaimer, the term of this patent is extended or adjusted under 35 U.S.C. 154(b) by 824 days.

(21) Appl. No.: 17/278,272

(22) PCT Filed: Dec. 17, 2019

(86) PCT No.: PCT/KR2019/017899
§ 371 (c)(1),
(2) Date: Mar. 19, 2021

(87) PCT Pub. No.: WO2020/130580
PCT Pub. Date: Jun. 25, 2020

(65) Prior Publication Data
US 2021/0346308 A1  Nov. 11, 2021

(30) Foreign Application Priority Data
Dec. 17, 2018  (KR) .................. 10-2018-0163379

(51) Int. Cl.
| | |
|---|---|
| *C08G 81/00* | (2006.01) |
| *A61K 9/51* | (2006.01) |
| *A61K 31/704* | (2006.01) |
| *A61K 35/15* | (2015.01) |
| *A61K 35/17* | (2015.01) |
| *A61K 47/34* | (2017.01) |
| *A61P 35/00* | (2006.01) |
| *C08G 65/333* | (2006.01) |
| *C08G 73/02* | (2006.01) |
| *C08G 81/02* | (2006.01) |

(52) U.S. Cl.
CPC .......... *A61K 9/5146* (2013.01); *A61K 31/704* (2013.01); *A61K 35/15* (2013.01); *A61K 35/17* (2013.01); *A61K 47/34* (2013.01); *A61P 35/00* (2018.01); *C08G 65/33317* (2013.01); *C08G 65/33331* (2013.01); *C08G 73/0273* (2013.01); *C08G 81/00* (2013.01); *C08G 81/025* (2013.01)

(58) Field of Classification Search
None
See application file for complete search history.

(56) References Cited

U.S. PATENT DOCUMENTS

| | | | | |
|---|---|---|---|---|
| 2010/0233264 A1* | 9/2010 | Lee | .................. | C08G 65/33324 424/85.4 |
| 2010/0266491 A1 | 10/2010 | Farokhzad et al. | | |
| 2011/0151566 A1 | 6/2011 | Hedrick et al. | | |
| 2013/0330278 A1* | 12/2013 | Gao | .................. | G01N 21/6486 424/9.6 |
| 2016/0331845 A1* | 11/2016 | Mao | .................. | A61K 47/6803 |
| 2021/0346308 A1* | 11/2021 | Kim | ...................... | C08G 81/00 |

FOREIGN PATENT DOCUMENTS

| | | | |
|---|---|---|---|
| CN | 204824845 | U | 12/2015 |
| CN | 105494312 | A | 4/2016 |
| EP | 3 530 291 | A1 | 8/2019 |
| JP | 2013079381 | A | 5/2013 |
| JP | 2913079381 | A | 5/2013 |
| KR | 1020050047763 | A | 5/2005 |
| KR | 10-2008-0095130 | A | 10/2008 |
| KR | 1020110114914 | A | 10/2011 |
| KR | 1020120051495 | A | 5/2012 |
| KR | 1020150099655 | A | 9/2015 |
| KR | 1020170111181 | A | 10/2017 |
| KR | 1020180033533 | A | 4/2018 |
| WO | 2008/130180 | A1 | 10/2008 |
| WO | 2009031861 | A2 | 3/2009 |
| WO | 2012/040513 | A1 | 3/2012 |
| WO | 2013/152059 | A1 | 10/2013 |

OTHER PUBLICATIONS

Shen; Poly(ethylene glycol)-block-poly(D, L-lactide acid) micelles anchored with angiopep-2 for brain-targeting delivery; Journal of Drug Targeting, 2011; 19(3) pp. 197-203. (Year: 2011).*
International Search Report and Written Opinion, mailed Apr. 10, 2020, for International Application No. PCT/KR2019/017899, 14 pages. (with English Translation of the International Search Report).
Kim et al., "Verteporfin-loaded poly(ethylene glycol)-poly(beta-amino ester)-poly(ethylene glycol) triblock micelles for cancer therapy," *Biomacromolecules* 19(8):3361-3370, 2018. (21 pages).
Ko et al., "Tumoral acidic extracellular pH targeting of pH-responsive MPEG-poly (β-amino ester) block copolymer micelles for cancer therapy," *Journal of Controlled Release* 123:109-115, 2007.
Li et al., "A novel application of maleimide for advanced drug delivery: in vitro and in vivo evaluation of maleimide-modified pH-sensitive liposomes," *International Journal of Nanomedicine* 8:3855-3866, 2013.
Nasongkla et al., "Multifunctional Polymeric Micelles as Cancer-Targeted, MRI-Ultrasensitive Drug Delivery Systems," *Nano Letters* 6(11):2427-2430, 2006.
Stephan et al., "Therapeutic cell engineering using surface-conjugated synthetic nanoparticles," *Nat. Med.* 16(9):1035-1041, 2010. (17 pages).
Office Action Issued in Chinese Patent Application No. 201980070001.4 on May 8, 2023.

(Continued)

*Primary Examiner* — David J Buttner
(74) *Attorney, Agent, or Firm* — HULTQUIST, PLLC; Steven J. Hultquist

(57) ABSTRACT

The present invention relates to a block copolymer, comprising a hydrophilic first block, a hydrophobic second block, and a functional group capable of specifically binding to thiol.

18 Claims, 19 Drawing Sheets

(56) References Cited

OTHER PUBLICATIONS

English Translation of Office Action Issued in Chinese Patent Application No. 201980070001.4 on May 8, 2023.
First Office Action in CN201980070001.4, Jul. 11, 2022.
First Office Action in CN201980070001.4, Jul. 11, 2022, English Translation.
Search Report in CN201980070001.4, Jul. 5, 2022, English Translation.
Jing, Y., et al., "Optimization and reparation of mal-PEG-PCL drug-loading nanoparticles by the response surface methodology", New Chemical Materials, 2016, pp. 204-206, vol. 44, No. 2.
Jing, Y., et al., "Optimization and reparation of mal-PEG-PCL drug-loading nanoparticles by the response surface methodology", New Chemical Materials, 2016, pp. 204-206, vol. 44, No. 2, English Translation.
Sadeqzadeh, E., et al., "Combined MUC1-specific nanobody-tagged PEG-polyethylenimine polyplex targeting and transcriptional targeting of tBid transgene for directed killing of MUC1 over-expressing tumour cells", Journal of Controlled Release, 2011, pp. 85-91, vol. 156, Publisher: Elsevier.
Gil, M.S., et al., "Bioengineered robust hybrid hydrogels enrich the stability and efficacy of biological drugs", Journal of Controlled Release, 2017, pp. 119-132, vol. 267, Publisher: Elsevier.

\* cited by examiner

[FIG. 6]
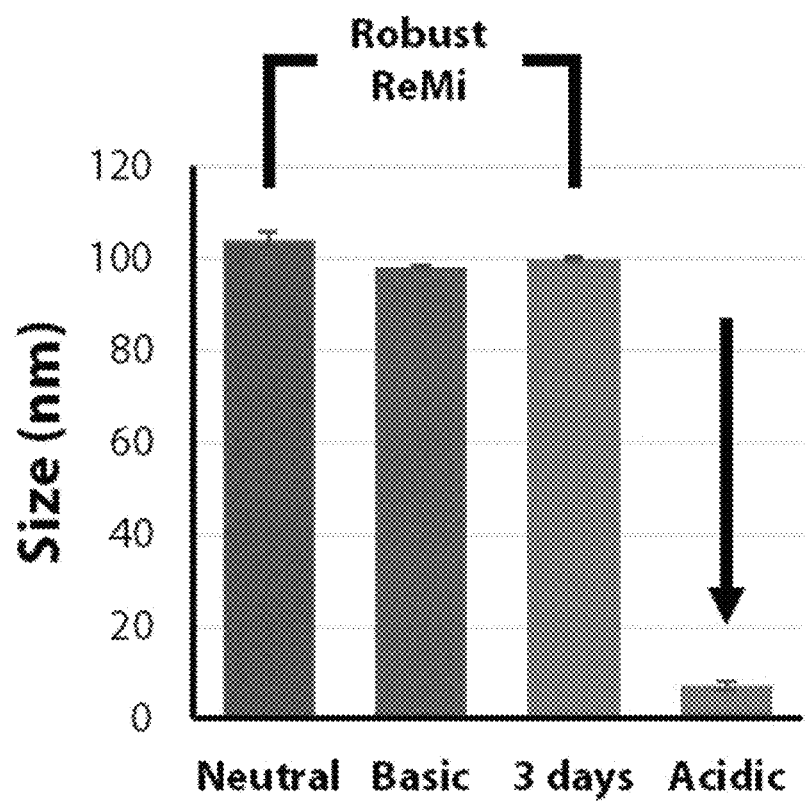

[FIG. 7]
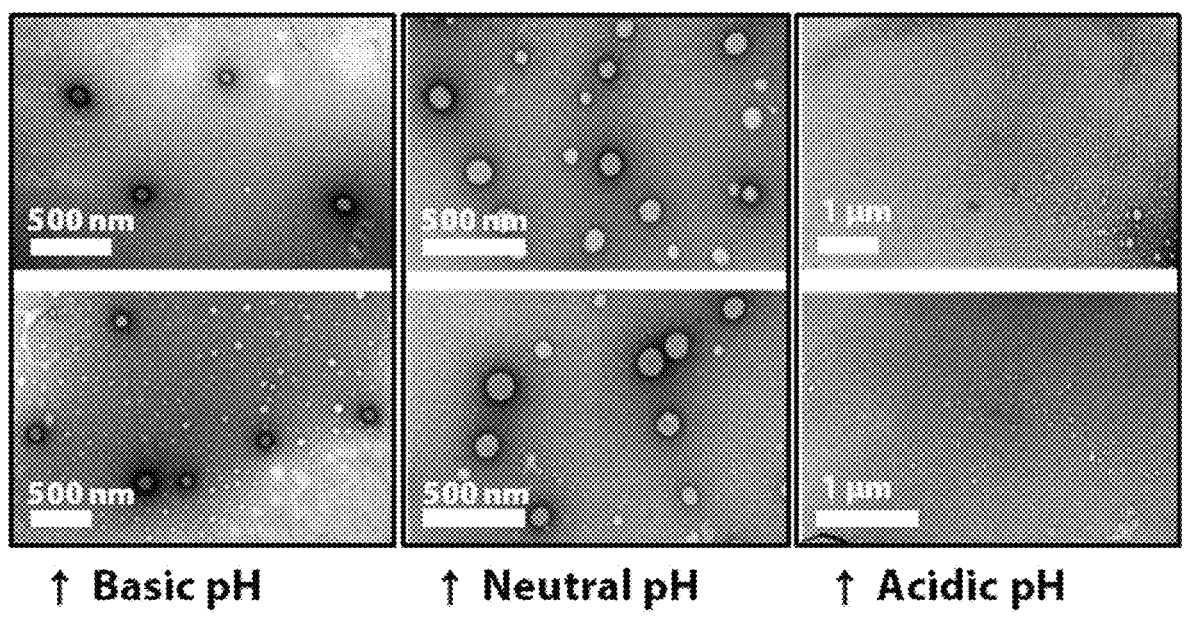

[FIG. 8]
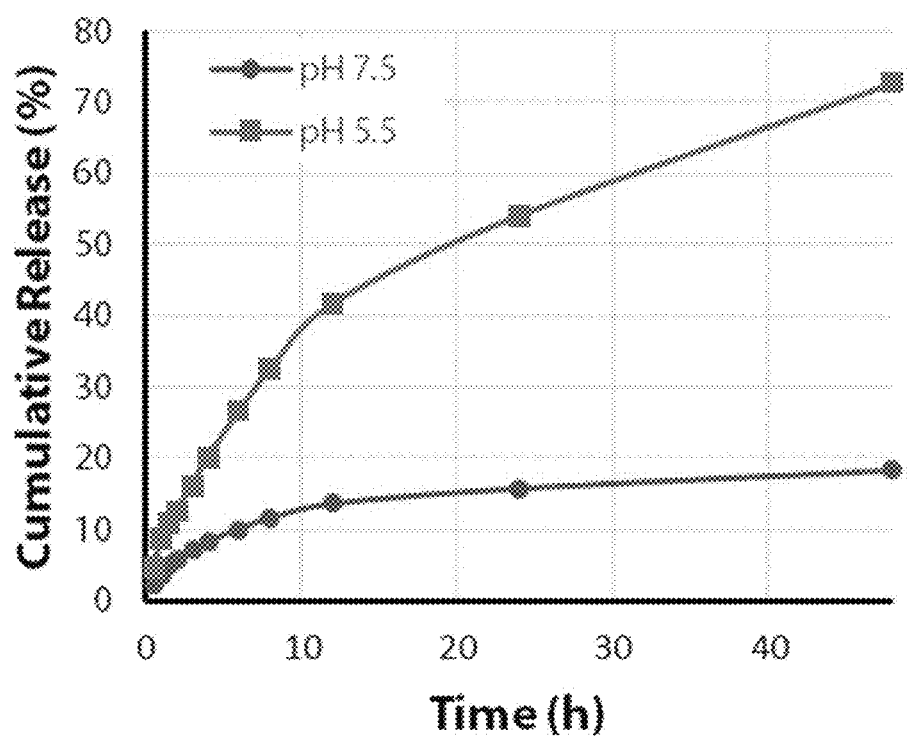

[FIG. 9]
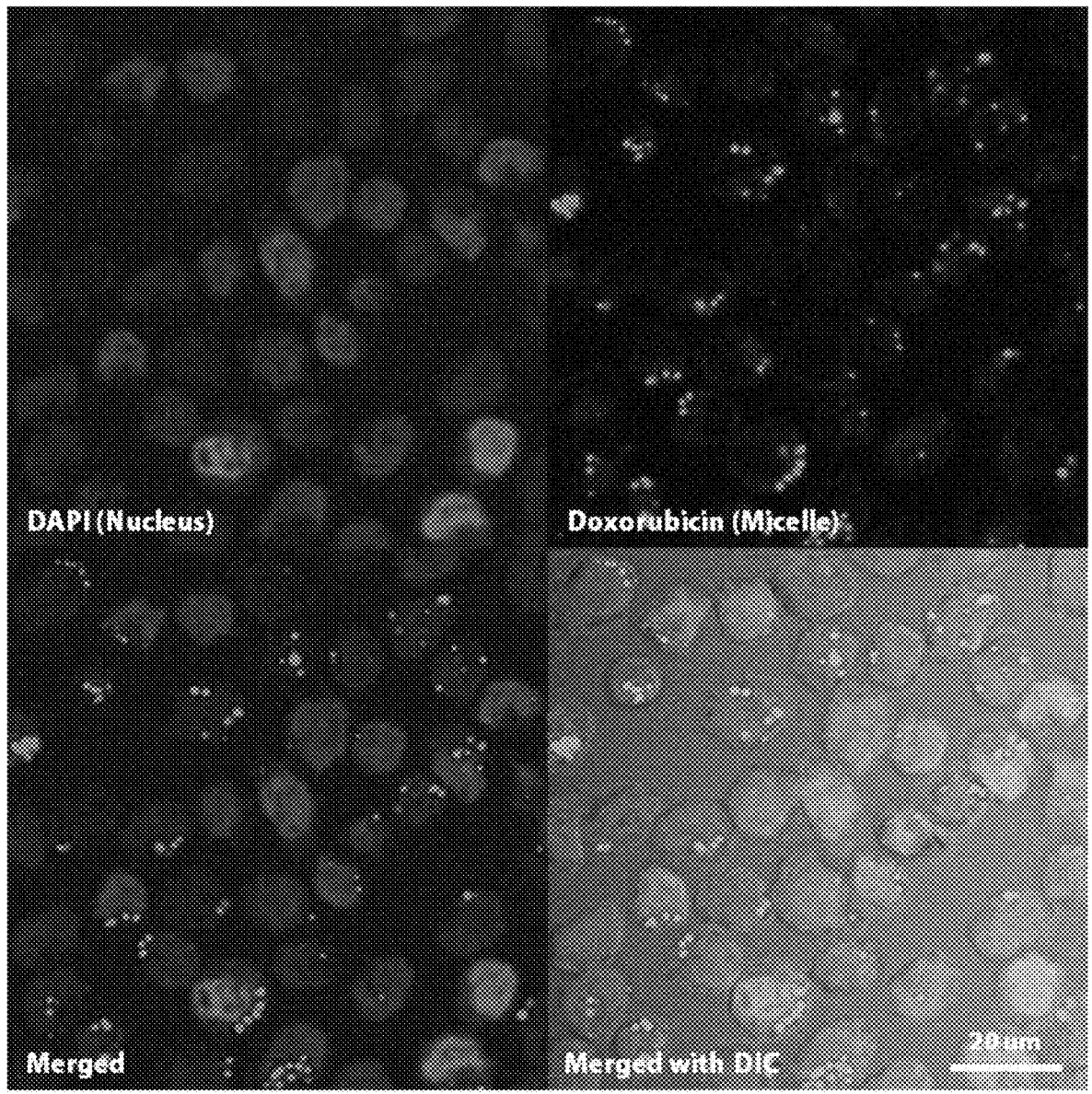

[FIG. 10]
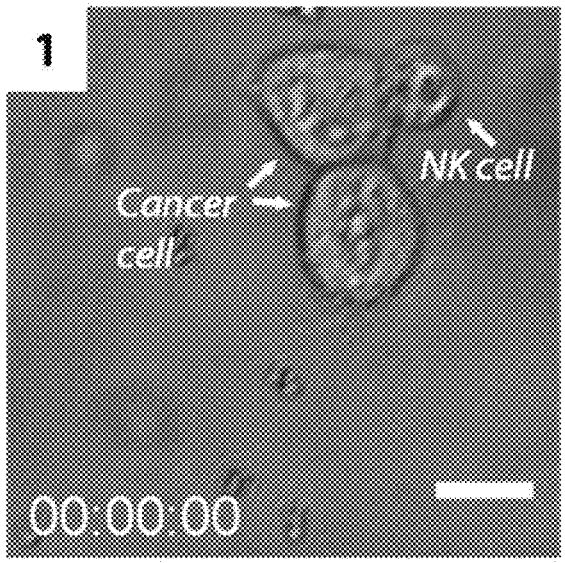
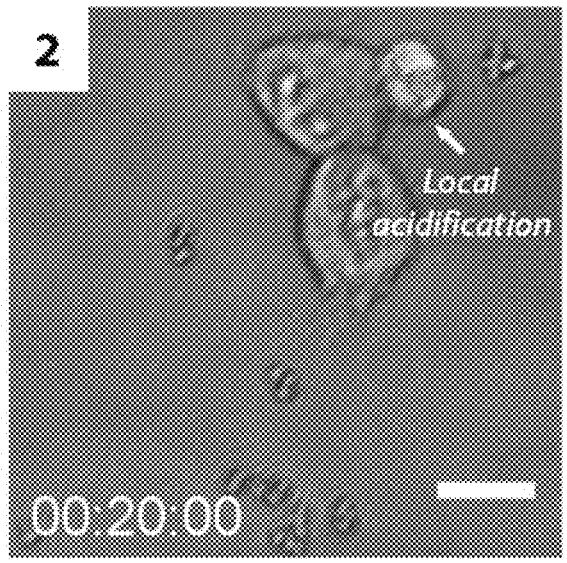
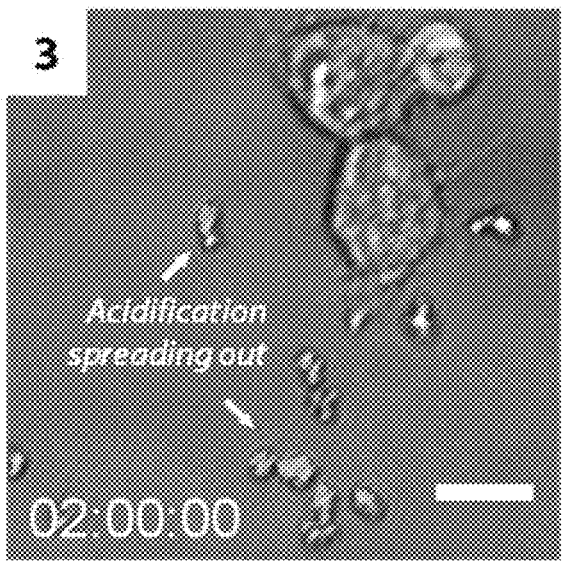
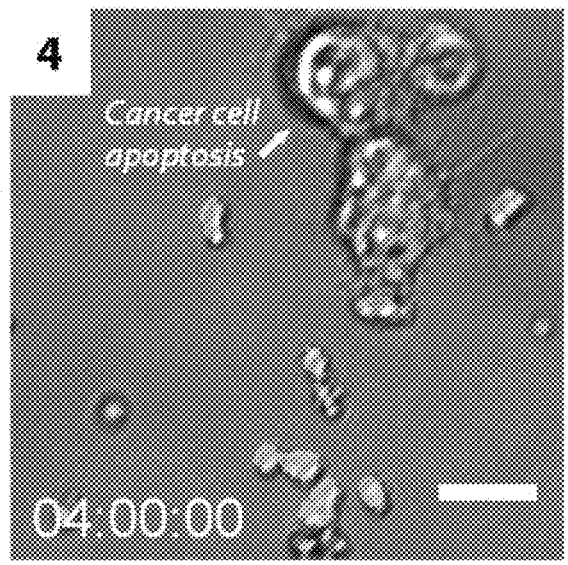

[FIG. 11]
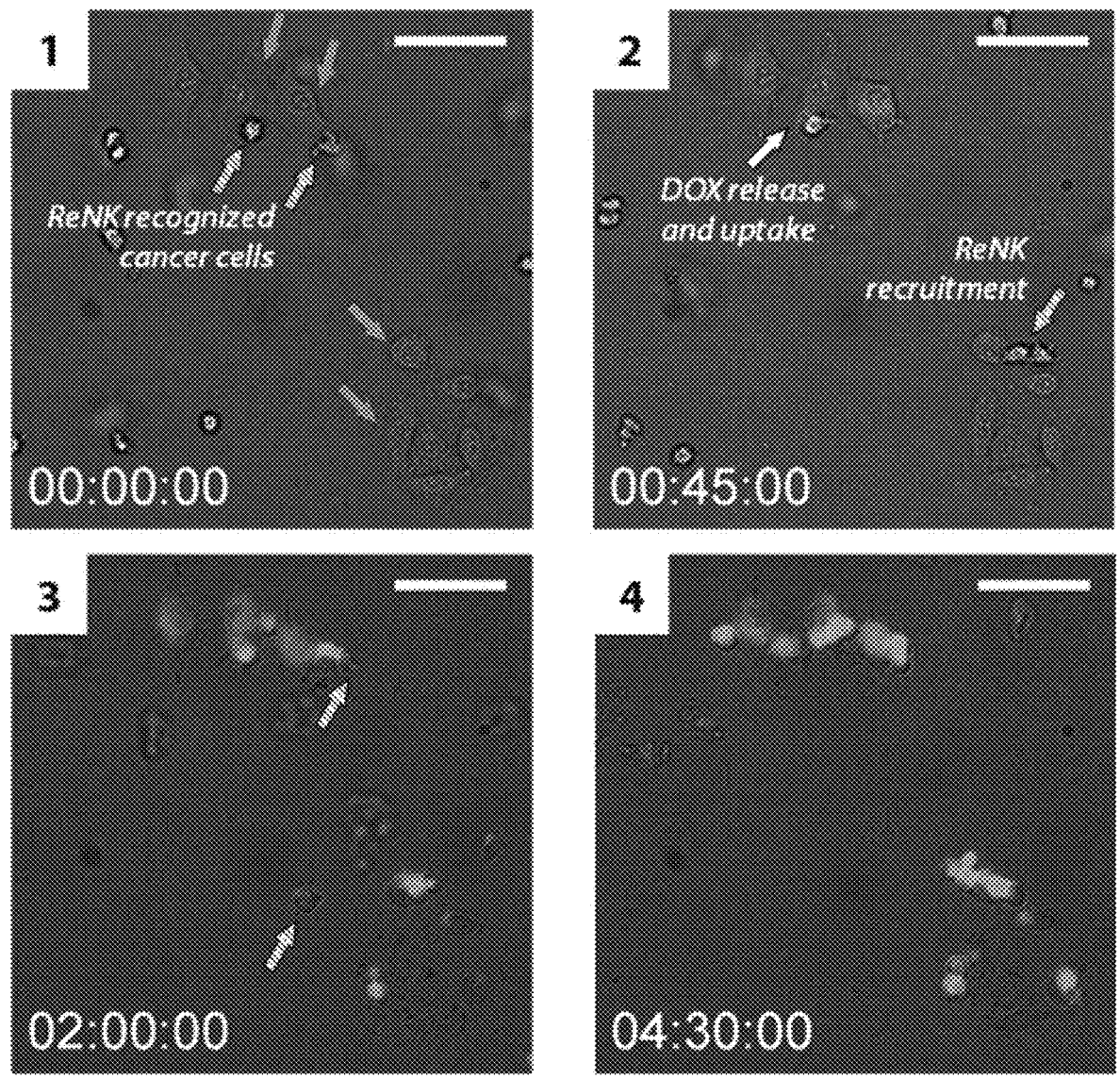

[FIG. 12]
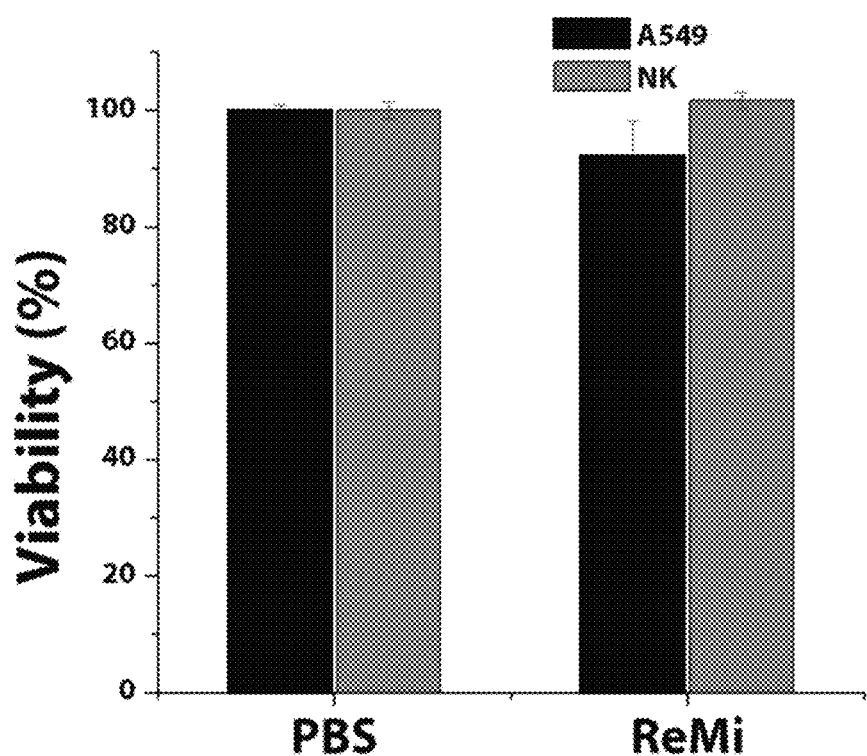

[FIG. 13]
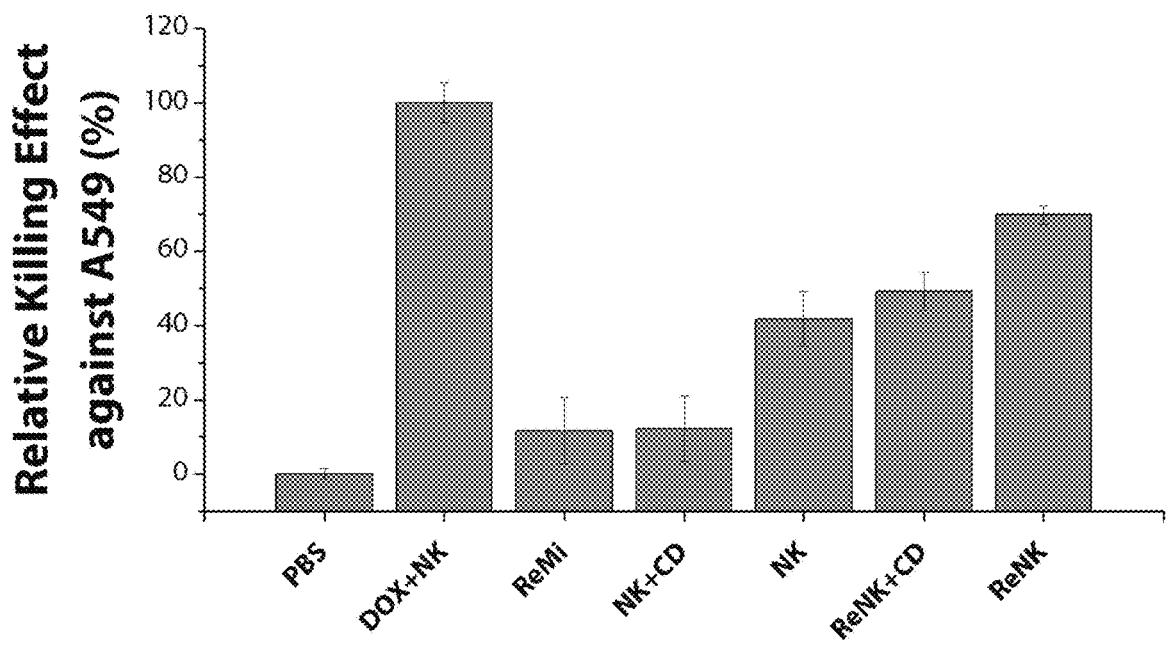

[FIG. 14]
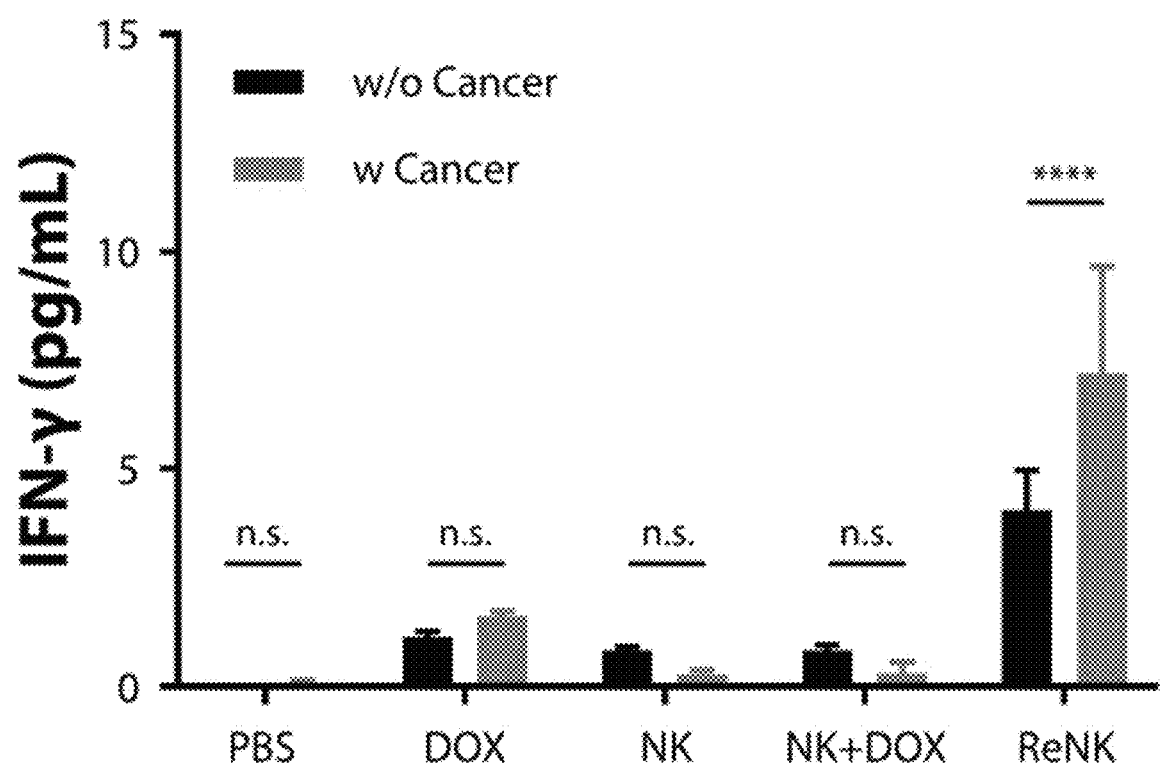

[FIG. 15]
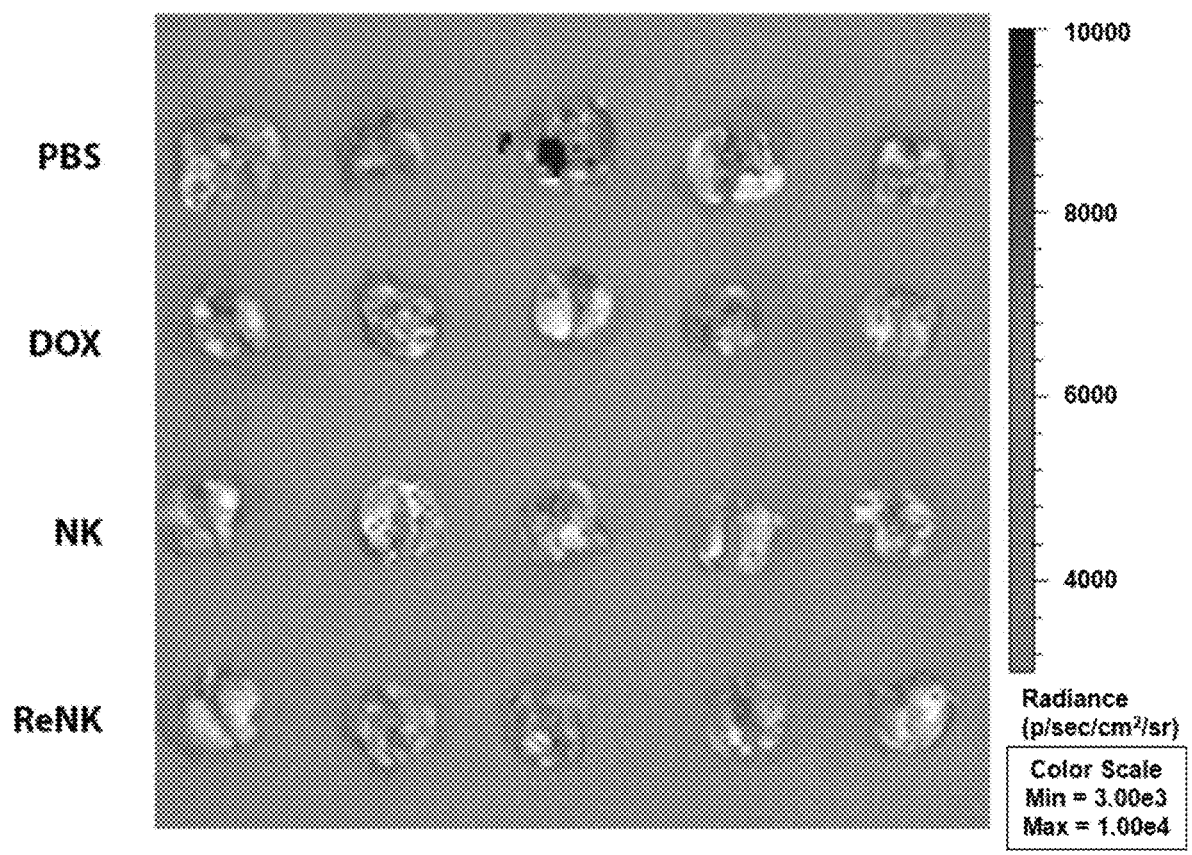

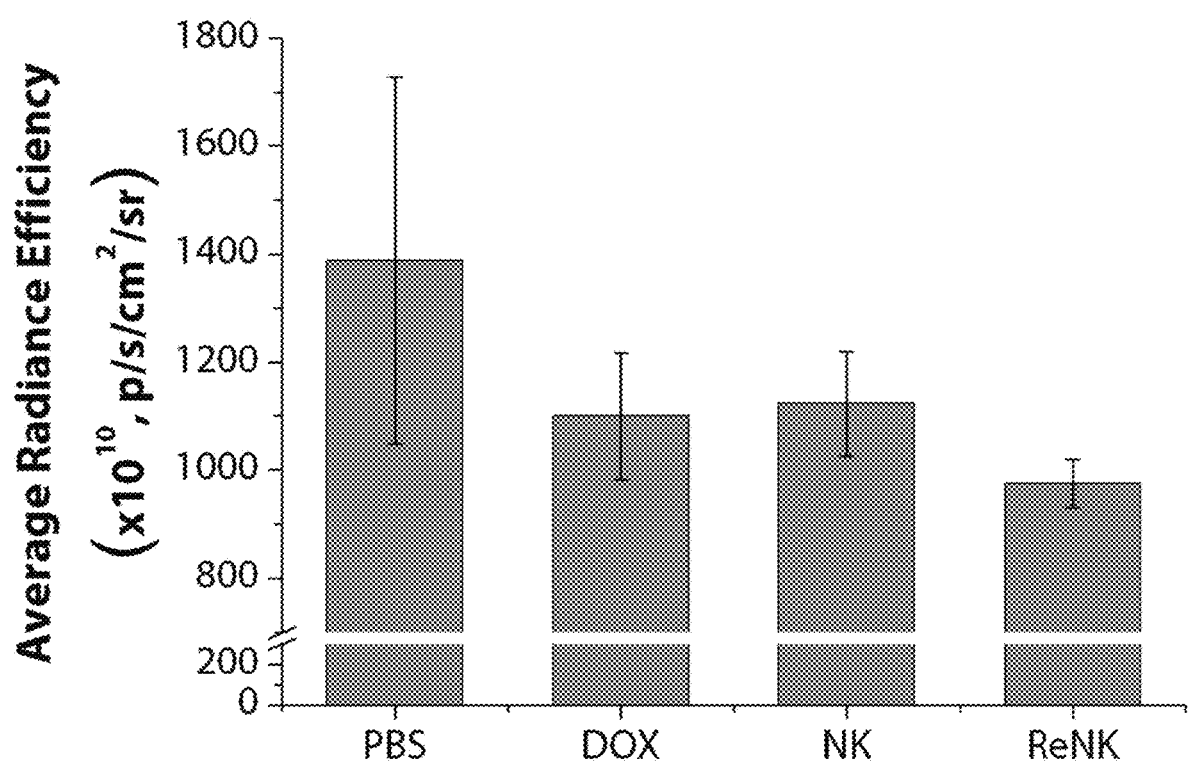
[FIG. 16]

[FIG. 17]
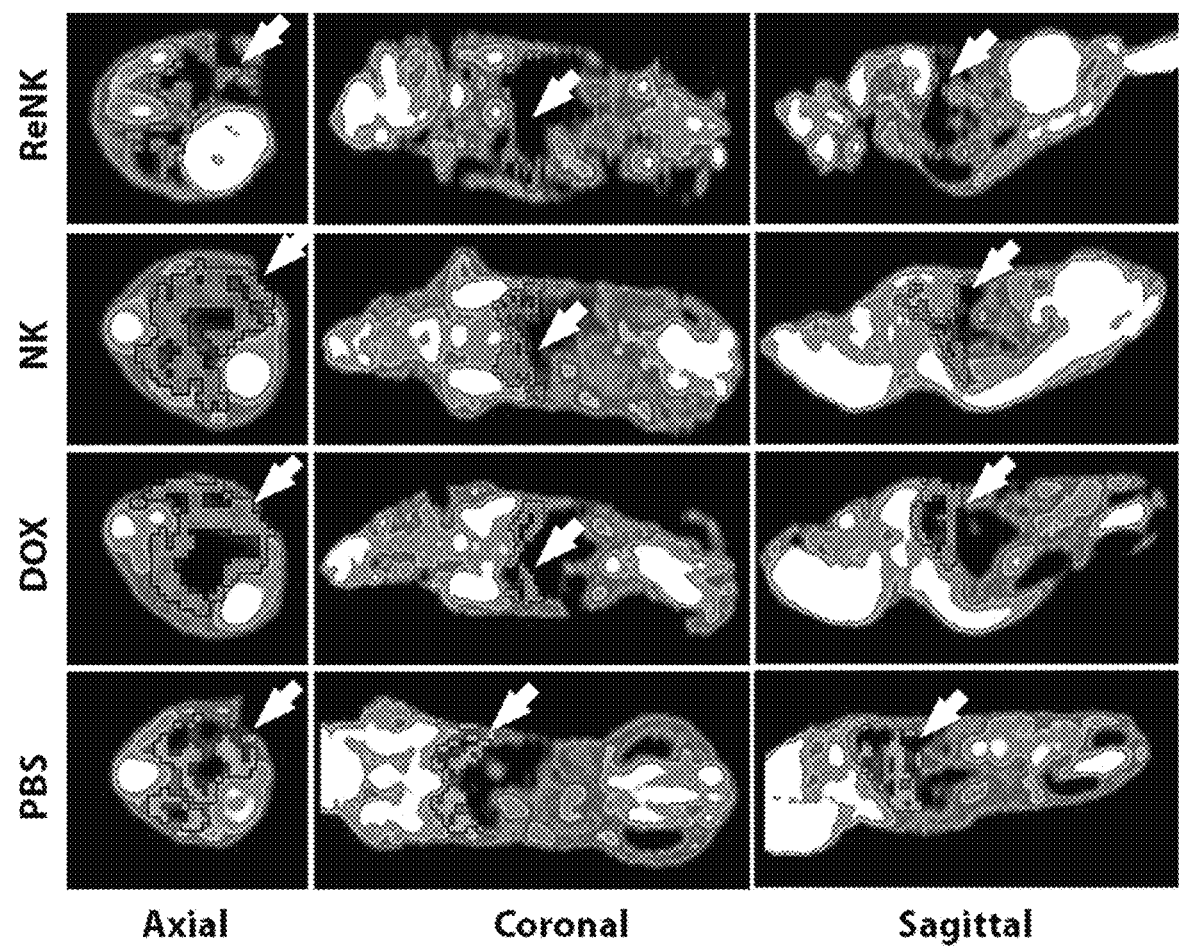

[FIG. 18]
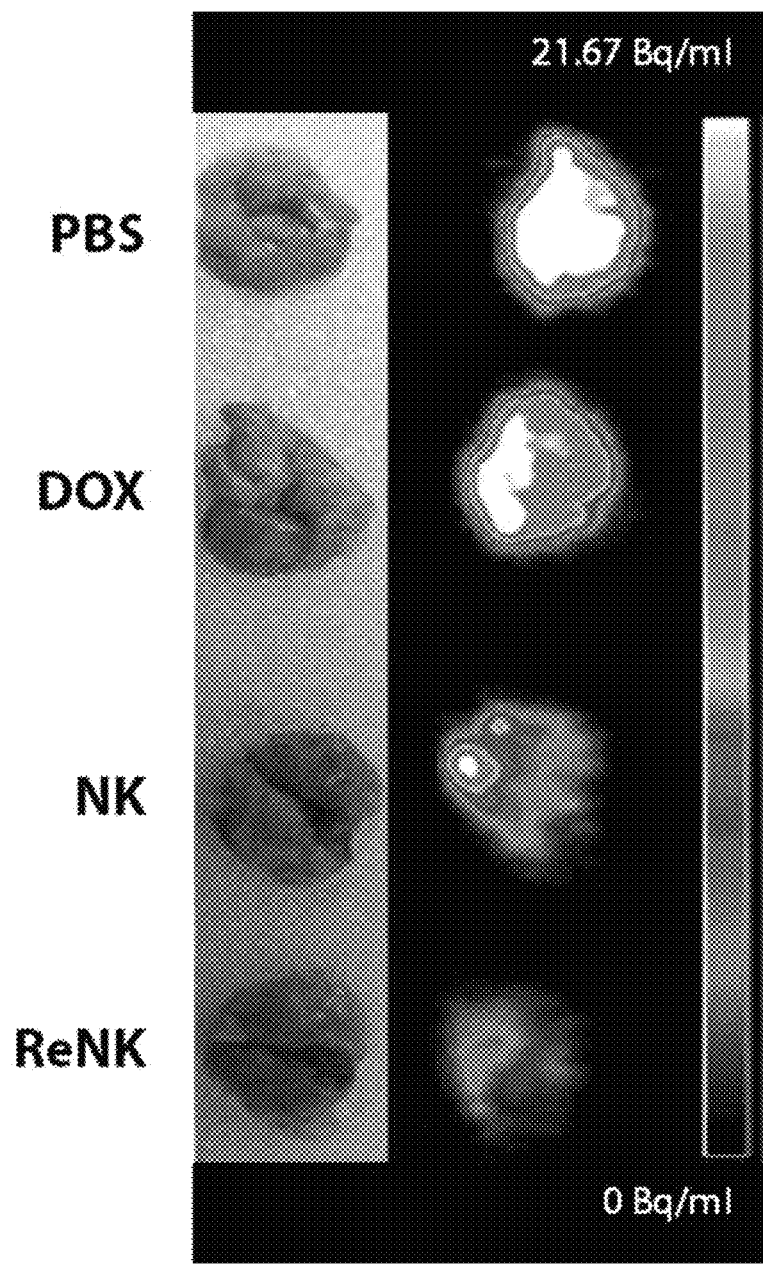

[FIG. 19]
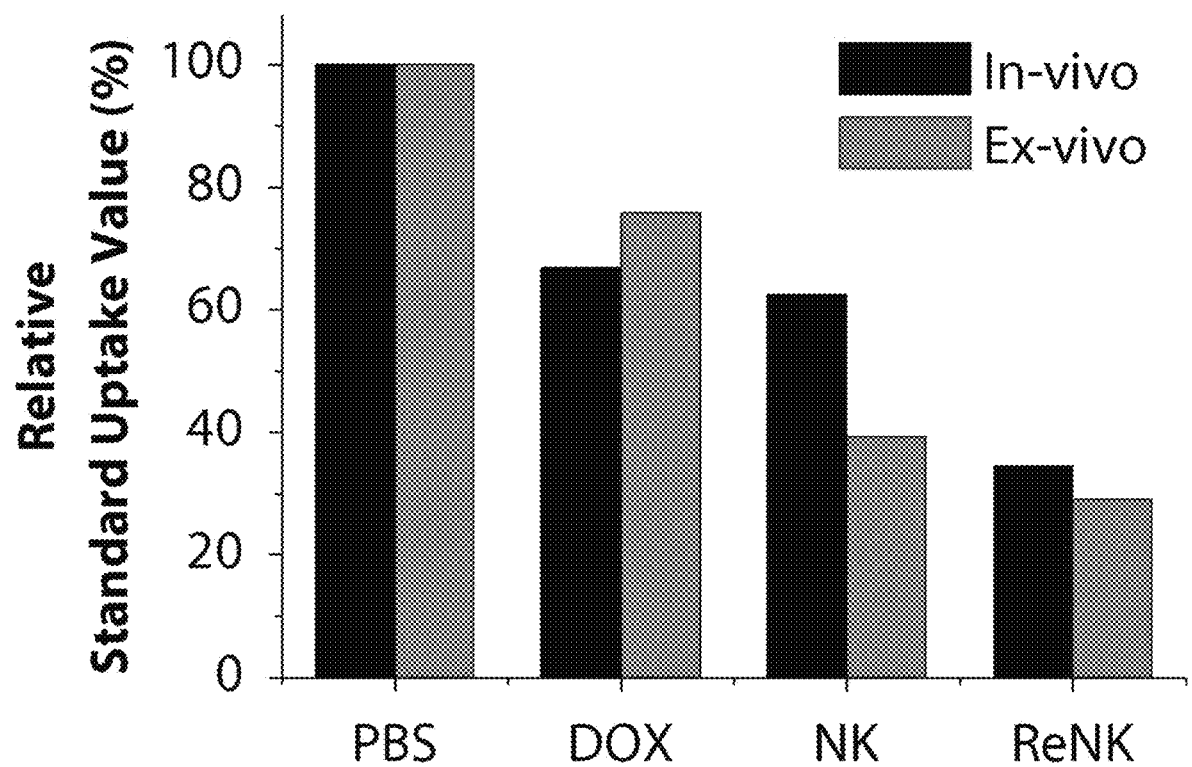

BLOCK COPOLYMER COMPRISING HYDROPHILIC FIRST BLOCK, HYDROPHOBIC SECOND BLOCK, AND FUNCTIONAL GROUP CAPABLE OF SPECIFICALLY BINDING TO THIOL

TECHNICAL FIELD

The present invention relates to a block copolymer, comprising a hydrophilic first block, a hydrophobic second block, and a functional group capable of specifically binding to thiol.

BACKGROUND ART

Anti-cancer chemotherapy and radiotherapy, which are widely known as therapeutic methods for treating cancer, a representative intractable disease of modern humans, cause non-specific pharmacological action throughout the patient's body, and thus have problems of poor therapeutic efficiency and of causing various side effects in patients.

In order to solve these problems, new therapeutic methods based on immune responses of the human body have recently emerged. Among these, T cells and natural killer cells have a specific mechanism of accurately recognizing and attacking cancer cells, and thus have the potential to treat cancer without damaging normal cells, unlike conventional anti-cancer chemo/radiation therapies.

However, immune cells alone have had difficulty reaching complete treatment of cancer due to immune evasion of cancer cells through their genetic variations, lack of toxicity of individual immune cells, and the like.

Therefore, in order to solve these problems, there is a need for a method of increasing therapeutic efficiency by allowing an anti-cancer chemical drug to act on cancer simultaneously with immune cells, and there is also a need for development of an intelligent drug delivery system to prevent an anti-cancer chemical drug from acting on normal tissues.

DISCLOSURE OF INVENTION

Technical Problem

In order to solve the above-described problems, the present inventors have prepared a block copolymer comprising a hydrophilic first block; a hydrophobic second block including a unit that is decomposed or becomes cationic at a condition of pH 4.5 to 7; and a functional group capable of specifically binding to thiol, and have identified that the block copolymer may be attached to thiol present on the surface of immune cells and may carry a drug and release the drug only at an acidic condition so that action of the immune cells is potentiated, thereby completing the present invention.

Accordingly, an object of the present invention is to provide a block copolymer that allows its carried-on drug to act simultaneously with immune cells and thus enables prevention or treatment of cancer diseases or disorders, or various infections.

Solution to Problem

In order to achieve the above object, according to an embodiment of the present invention, there is provided a block copolymer, comprising a hydrophilic first block; a hydrophobic second block; and a functional group capable of specifically binding to thiol, wherein the hydrophobic second block includes, in its main chain, a unit that is decomposed at a condition of pH 4.5 to 7, includes, in its main or side chain, a unit that becomes cationic at a condition of pH 4.5 to 7, or includes both units.

According to another embodiment of the present invention, there is provided a nanoparticle, comprising the block copolymer.

According to yet another embodiment of the present invention, there is provided a drug delivery vehicle, comprising the nanoparticle and a drug.

According to still yet another embodiment of the present invention, there is provided a modified cell, comprising the drug delivery vehicle and an immune cell.

According to still yet another embodiment of the present invention, there is provided a pharmaceutical composition for anti-cancer use, comprising the block copolymer and an anti-cancer drug.

In addition, according to still yet another embodiment of the present invention, there is provided a pharmaceutical composition for anticancer use or for preventing or treating infection, comprising the block copolymer, a drug, and an immune cell.

Advantageous Effects of Invention

The block copolymer according to the present invention can specifically bind to thiol present on the surface of immune cells and can undergo a structural change only at an acidic condition induced by the immune cells so that a drug is released. Thus, the block copolymer can potentiate, through chemotherapy, the immune cell's anti-cancer capacity or prophylactic or therapeutic capacity against infections while inhibiting non-specific side effects of its carried drug.

BRIEF DESCRIPTION OF DRAWINGS

FIG. 6 illustrates a graph showing average hydration sizes, depending on pH conditions, for a drug delivery vehicle according to an embodiment of the present invention.

FIG. 7 illustrates transmission electron microscopic images, depending on pH conditions, for the drug delivery vehicle according to the embodiment of the present invention.

FIG. 8 illustrates a graph showing drug release behaviors, depending on pH conditions, for the drug delivery vehicle according to the embodiment of the present invention.

FIG. 9 illustrates fluorescent images of the drug delivery vehicle according to the embodiment of the present invention which is attached to cells.

FIGS. 10 and 11 illustrate fluorescent images taken while the drug delivery vehicle according to the embodiment of the present invention is attached to natural killer cells and the natural killer cells recognize and attack cancer cells.

FIG. 12 illustrates results obtained by assessing cytotoxicity of the drug delivery vehicle according to the embodiment of the present invention.

FIG. 13 illustrates a graph showing a cancer cell-killing effect of the drug delivery vehicle according to the embodiment of the present invention.

FIG. 14 illustrates a graph obtained by measuring IFN-γ levels in a case where the drug delivery vehicle according to the embodiment of the present invention is administered to an animal cancer model.

FIGS. 15 to 19 illustrate results obtained by assessing a metastatic tumorigenicity inhibitory effect of the drug delivery system according to the embodiment of the present invention in a case where the drug delivery system is administered to an animal cancer model.

BEST MODE FOR CARRYING OUT THE INVENTION

Figure 1:
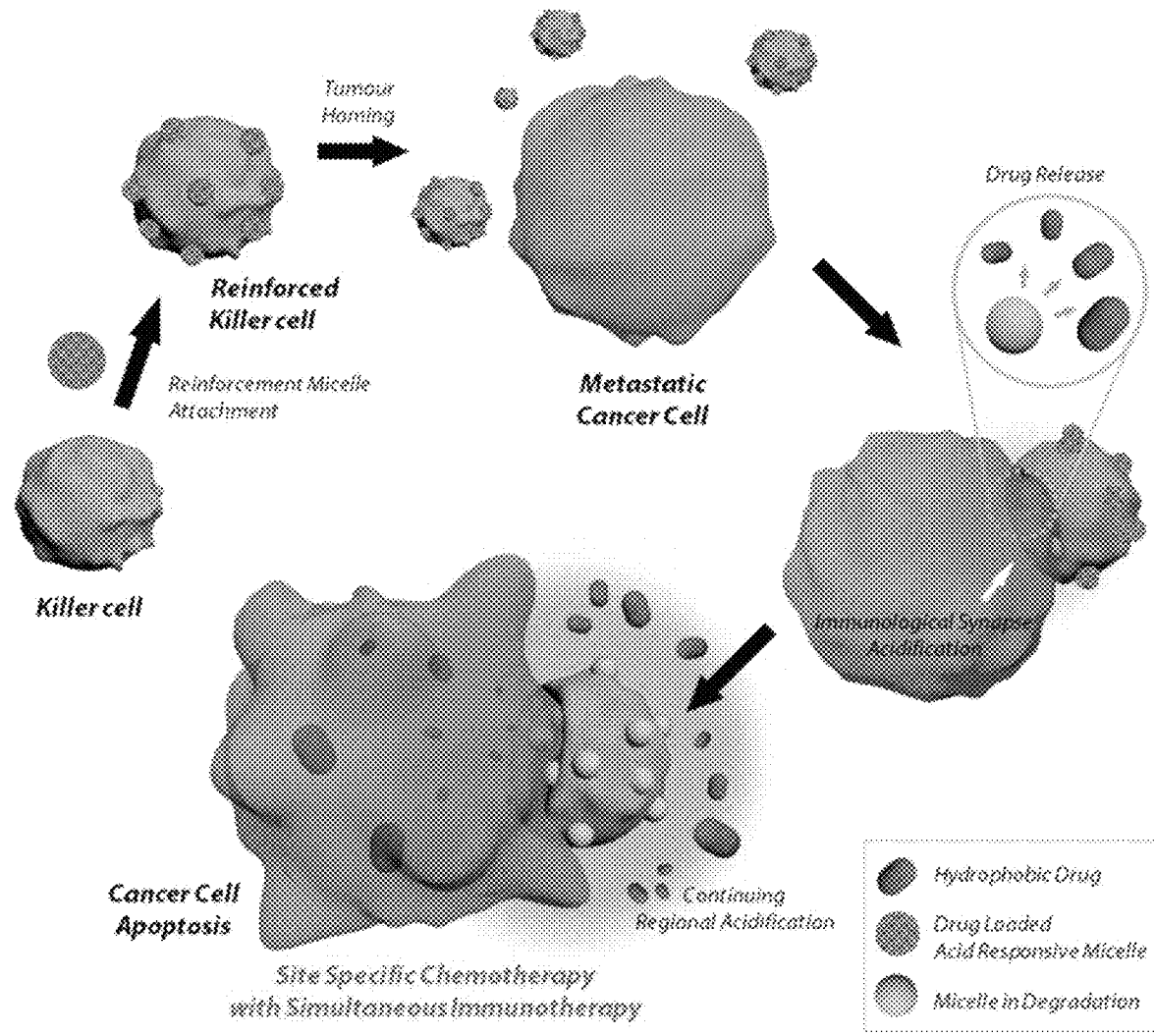
FIG. 1 illustrates a view simulating responses caused by a block copolymer according to an embodiment of the present invention in a case where the block copolymer is administered into the body.

In an aspect of the present invention, there is provided a block copolymer that undergoes a structural change at a low pH.

In an embodiment of the present invention, there is provided a block copolymer, comprising a hydrophilic first block; a hydrophobic second block; and a functional group capable of specifically binding to thiol, wherein the hydrophobic second block includes, in its main chain, a unit that is decomposed at a condition of pH 4.5 to 7, includes, in its main or side chain, a unit that becomes cationic at a condition of pH 4.5 to 7, or includes both units.

In an embodiment of the present invention, the hydrophilic first block may mean a polymer having high solubility in water. For example, the hydrophilic first block may not exhibit turbidity in a case of being dissolved, as a polymer, in water at room temperature. In addition, the hydrophilic first block may include poly(vinyl alcohol), poly(vinyl pyrrolidone), poly(acrylamide), poly(oxazoline), or poly(ether), or a copolymer thereof. Specifically, the hydrophilic first block is poly(ether) and may include poly(ethylene glycol), dextran, mannan, pullulan, or cellulose, or a copolymer thereof. More specifically, the hydrophilic first block may include poly(ethylene glycol).

In addition, the hydrophilic first block may include, consist essentially of, or consist of a unit represented by Formula 1.

[Formula 1]

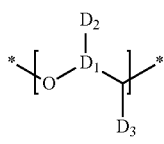

In the formula, $D_1$ is a $C_1$ or $C_2$ alkylene group, and $D_2$ and $D_3$ are each independently selected from hydrogen; halogen; a hydroxyl group; and a methyl group.

Meanwhile, in an embodiment of the present invention, the hydrophobic second block may mean a polymer having low solubility in water. For example, the hydrophobic second block may exhibit turbidity in a case of being dissolved in water at room temperature. In addition, the hydrophobic second block may include, in its main chain, a unit that is decomposed at a condition of pH 4.5 to 7, include, in its main or side chain, a unit that becomes cationic at a condition of pH 4.5 to 7, or include both units.

Specifically, the hydrophobic second block may include, in its main chain, a unit that is decomposed at a condition of pH 5.8 to 6.8, include, in its main or side chain, a unit that becomes cationic at a condition of pH 5.8 to 6.8, or include both units. Here, the unit that becomes cationic at an acidic condition, for example, at a condition of pH 4.5 to 7.0 or pH 5.8 to 6.8, may be a unit whose conjugate acid has pKa of 4.5 to 7.0 or 5.8 to 6.8. Also here, the unit that is decomposed or becomes cationic at an acidic condition may be a unit that is not decomposed or does not become cationic at a non-acidic condition, such as a condition of more than pH 7.0 or more than pH 6.8.

Due to inclusion of such a unit that is decomposed or becomes cationic at an acidic condition, the block copolymer of the present invention may undergo a structural change as a hydrophilic/hydrophobic balance is collapsed in a case where a hydrophobic group becomes cationic at an acidic condition, such as a condition of pH 4.5 to 7.0 or pH 5.8 to 6.8, or as the hydrophobic group is decomposed. Thus, in a case of carrying a drug, the block copolymer of the embodiment of the present invention may have a feature of selectively releasing the drug at an acidic condition. In particular, in a case of being administered to a subject, the block copolymer may bind to immune cells already present in the subject, or to immune cells added additionally to the subject, and thus may selectively release a drug in an acidic environment that forms when the immune cells play their role. As such, the block copolymer of the present invention may potentiate the immune cell's capacity while inhibiting non-specific side effects of its carried-on drug.

Specifically, in the hydrophobic second block, a polymer including a unit that is decomposed at an acidic condition, such as a condition of pH 4.5 to 7.0 or pH 5.8 to 6.8, may include poly(lactide), poly(glycolide), poly(acetal), poly(ketal), or poly(aminoester), or a copolymer thereof. In addition, a polymer including a unit that becomes cationic at an acidic condition, such as pH 4.5 to 7.0 or pH 5.8 to 6.8, may include poly(ethylene imine), poly(propylene imine), poly(aminoester), poly(amidoamine), poly(dimethylaminoethyl methacrylate), poly(lysine), chitosan, or gelatin, or a copolymer thereof. More specifically, the hydrophobic second block may include poly(aminoester) as a polymer including both unit that is decomposed at an acidic condition and unit that becomes cationic at an acidic condition. More specifically, the hydrophobic second block may include, consist essentially of, or consist of a unit represented by Formula 2.

[Formula 2]

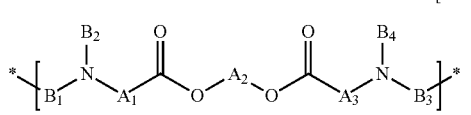

In the formula, $A_1$ and $A_3$ are each independently selected from a $C_1$ to $C_5$ linear or branched alkylene group; a $C_2$ to $C_5$ linear or branched alkenylene group; and a $C_2$ to $C_5$ linear or branched alkynylene group, $A_2$ is selected from a $C_1$ to $C_{10}$ linear or branched alkylene group; a $C_2$ to $C_{10}$ linear or branched alkenylene group; and a $C_2$ to $C_{10}$ linear or branched alkynylene group, and $B_1$ and $B_3$ are each independently selected from a $C_1$ to $C_{10}$ linear or branched alkylene group; a $C_2$ to $C_{10}$ linear or branched alkenylene group; and a $C_2$ to $C_{10}$ linear or branched alkynylene group, and $B_2$ and $B_4$ are each independently selected from hydrogen; halogen; a $C_1$ to $C_{10}$ linear or branched alkyl group; a $C_2$ to $C_{10}$ linear or branched alkenyl group; a $C_2$ to $C_{10}$ linear or branched alkynyl group; a $C_1$ to $C_{10}$ linear or branched alkylene group; a $C_2$ to $C_{10}$ linear or branched alkenylene group; and a $C_2$ to $C_{10}$ linear or branched alkynylene group, wherein $B_1$ and $B_2$ may be connected to each other to form a $C_3$ to $C_{20}$ alicyclic or aromatic ring, and $B_3$ and $B_4$ may be connected to each other to form a $C_3$ to $C_{20}$ alicyclic or aromatic ring.

More specifically, in the formula, $A_1$ and $A_3$ may each independently be a $C_1$ to $C_5$ linear or branched alkylene group. $A_2$ may be a $C_1$ to $C_{10}$ linear or branched alkylene group. $B_1$ and $B_3$ may each independently be a $C_1$ to $C_{10}$ linear or branched alkylene group. $B_2$ and $B_4$ may each independently be selected from hydrogen; a $C_1$ to $C_{10}$ linear or branched alkyl group; and a $C_1$ to $C_{10}$ linear or branched alkylene group. $B_1$ and $B_2$ may be connected to each other to form a $C_4$ to $C_{10}$ alicyclic ring. $B_3$ and $B_4$ may be connected to each other to form a $C_4$ to $C_{10}$ alicyclic ring. More specifically, in the formula, $A_1$ and $A_3$ are each independently a $C_1$ to $C_5$ linear or branched alkylene group, $A_2$ is a $C_1$ to $C_{10}$ linear or branched alkylene group, $B_1$ and $B_3$ are each independently a $C_1$ to $C_{10}$ linear or branched alkylene group, and $B_2$ and $B_4$ are each independently selected from hydrogen; a $C_1$ to $C_{10}$ linear or branched alkyl group; and a $C_1$ to $C_{10}$ linear or branched alkylene group, wherein $B_1$ and $B_2$ may be connected to each other to form a $C_4$ to $C_{10}$ alicyclic ring, and $B_3$ and $B_4$ may be connected to each other to a $C_4$ to $C_{10}$ alicyclic ring.

In an embodiment of the present invention, the functional group capable of specifically binding to thiol may be, for example, a disulfide group, a maleimide group, an alkenyl group, or an alkynyl group, or a combination thereof Alternatively, the functional group may be a derivative of the disulfide group, a derivative of the maleimide group, a derivative of the alkenyl group, or a derivative of the alkynyl group, or a combination thereof Here, the derivative of the disulfide group may mean a functional group formed by binding a protecting group to the disulfide group. Here, unless otherwise stated, the alkenyl group or alkynyl group may respectively mean, but is not limited to, a functional group that has 2 to 60 carbon atoms, has a double bond or triple bond, and includes a linear or branched chain group. The functional group capable of specifically binding to thiol may specifically be a maleimide group or a derivative thereof.

More specifically, the block copolymer of the embodiment of the present invention may include poly(ether) as the hydrophilic first block, include poly(aminoester) as the hydrophobic second block, and include a functional group capable of specifically binding to thiol.

More specifically, the block copolymer of the embodiment of the present invention may include a hydrophilic first block including the unit represented by Formula 1, include a hydrophobic second block including the unit represented by Formula 2, and include a functional group capable of specifically binding to thiol.

For example, the block copolymer is represented by Formula 3 and may include a functional group capable of specifically binding to thiol.

[Formula 3]

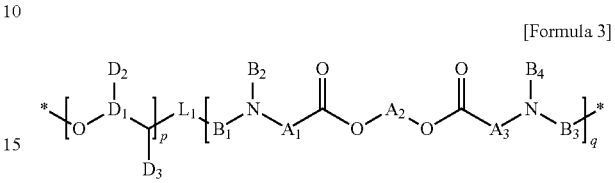

In the formula, $A_1$ to $A_3$ and $B_1$ to $B_4$ are as described for Formula 2, and $D_1$ to $D_3$ are as described for Formula 1. $L_1$ is a linker, and p and q are each independently an integer of 1 to 100. Specifically, p and q may each independently be an integer of 5 to 100. More specifically, p may be an integer of 10 to 80, or an integer of 20 to 70, and q may be an integer of 1 to 30, or an integer of 5 to 25. However, p and q are not particularly limited thereto. In addition, p/q may be (1:5) to (5:1). Specifically, p/q may be (1:1) to (5:1).

On the other hand, the linker $L_1$ may connect the hydrophilic first block and the hydrophobic second block to each other, and is not particularly limited as long as the linker $L_1$ does not inhibit an effect of the block copolymer of the present invention. A molecular weight of the linker $L_1$ is also not particularly limited as long as the linker $L_1$ does not inhibit an effect of the block copolymer of the present invention, and may be, for example, 10 to 2,000 Da, 10 to 1,800 Da, 10 to 1,600 Da, or 20 to 1,000 Da. The linker $L_1$ may have a structure derived from a compound/functional group commonly used to connect two or more polymers to each other. For example, $L_1$ may be represented by Formula 4.

[Formula 4]

In the formula, $B_3$ and $B_4$ are as described for Formula 2, and $E_1$ is a unit derived from a functional group capable of reacting with an amine Examples of the functional group capable of reacting with amine may include an alkenyl group, an alkynyl group, or an acrylate group, and examples of the unit derived from the functional group capable of reacting with amine may include *—$C_2H_4$—*, *—$C_2H_2$—*, and *—OOC—$C_2H_4$—*. However, a structure of $L_1$ is not particularly limited thereto.

Alternatively, for example, the block copolymer is represented by Formula 5 and may include a functional group capable of specifically binding to thiol.

[Formula 5]

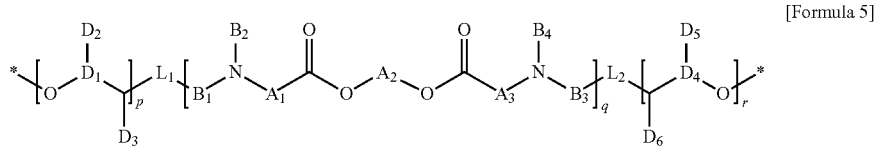

In the formula, $A_1$ to $A_3$ and $B_1$ to $B_4$ are as described for Formula 2, $D_1$ to $D_3$ are as described for Formula 1, and $L_1$ is as described for Formula 4. In addition, $D_1$ and $D_4$ may each independently be a $C_1$ or $C_2$ alkylene group, $D_2$, $D_3$, $D_5$, and $D_6$ may each independently be selected from hydrogen; halogen; a hydroxyl group; and a methyl group, $L_2$ may be a linker, and p, q, and r may each independently be an integer from 1 to 100, or an integer from 5 to 100. Specifically, (p+r)/q may be (1:10) to (10:1), (1:5) to (10:1), (1:3) to (10:1), or (1:1) to (10:1).

On the other hand, like $L_1$, the linker $L_2$ may connect the hydrophilic first block and the hydrophobic second block to each other, and is not particularly limited unless the linker $L_2$ inhibits an effect of the block copolymer of the present invention. A molecular weight of the linker $L_2$ is also as described for $L_1$, and the linker $L_2$ may have a structure derived from a compound/functional group commonly used to connect two or more polymers to each other. For example, $L_2$ may be represented by Formula 6.

[Formula 6]

In the formula, $B_1$ is selected from a $C_1$ to $C_{10}$ linear or branched alkylene group; a $C_2$ to $C_{10}$ linear or branched alkenylene group; and a $C_2$ to $C_{10}$ linear or branched alkynylene group, $B_2$ is selected from hydrogen; halogen; a $C_1$ to $C_{10}$ linear or branched alkyl group; a $C_2$ to $C_{10}$ linear or branched alkenyl group; a $C_2$ to $C_{10}$ linear or branched alkynyl group; a $C_1$ to $C_{10}$ linear or branched alkylene group; a $C_2$ to $C_{10}$ linear or branched alkenylene group; and a $C_2$ to $C_{10}$ linear or branched alkynylene group, and $E_2$ is a unit derived from a functional group capable of reacting with amine, wherein $B_1$ and $B_2$ may be connected to each other to form a $C_3$ to $C_{20}$ alicyclic or aromatic ring. $B_1$ and $B_2$ are as described in Formula 2.

Examples of the functional group capable of reacting with amine may include an alkenyl group, an alkynyl group, or an acrylate group, and examples of the unit derived from the functional group capable of reacting with amine may include *—$C_2H_4$—*, *—$C_2H_2$—*, and *—OOC—$C_2H_4$—*. However, a structure of $L_2$ is not particularly limited thereto.

The block copolymer according to an embodiment of the present invention may be specifically represented by Formula 7.

In the formula, p and r may each independently be an integer of 1 to 100, an integer of 5 to 100, an integer of 5 to 90, an integer of 10 to 80, an integer of 20 to 65, or an integer of 30 to 60, and q may be an integer of 1 to 60, an integer of 1 to 45, an integer of 1 to 30, an integer of 5 to 45, or an integer of 5 to 30.

Meanwhile, in the block copolymer according to the embodiment of the present invention, the hydrophilic first block may be contained in an amount of 1 to 99% by weight, 1 to 80% by weight, or 20 to 60% by weight, based on the total weight of the block copolymer. Specifically, the hydrophilic first block may be contained in, but is not limited to, an amount of 20 to 55% by weight, 25 to 60% by weight, 25 to 55% by weight, 25 to 50% by weight, 30 to 55% by weight, 30 to 50% by weight, 30 to 45% by weight, 35 to 50% by weight, or 35 to 45% by weight. In addition, based on the total weight of the block copolymer, the hydrophobic second block may be contained in an amount of 1 to 99% by weight, 10 to 90% by weight, or 40 to 80% by weight, and may be specifically contained in an amount of 40 to 75% by weight, 45 to 80% by weight, 45 to 75% by weight, 45 to 70% by weight, 50 to 75% by weight, 50 to 70% by weight, 50 to 65% by weight, 55 to 70% by weight, or 55 to 65% by weight. On the other hand, based on the total weight of the block copolymer, the functional group capable of specifically binding to thiol may be contained in an amount of 0.01 to 10% by weight or 0.01 to 5% by weight, and may be specifically contained in an amount of 0.05 to 5% by weight, 0.1 to 5% by weight, 0.5 to 5% by weight, or 1 to 4% by weight.

For example, in the block copolymer according to the embodiment of the present invention, based on the total weight of the block copolymer, poly(ether) or the unit represented by Formula 1 as a hydrophilic first block may be contained in an amount of 1 to 99% by weight, 1 to 80% by weight, or 20 to 60% by weight, and may be specifically contained in an amount of 20 to 55% by weight, 25 to 60% by weight, 25 to 55% by weight, 25 to 50% by weight, 30 to 55% by weight, 30 to 50% by weight, 30 to 45% by weight, 35 to 50% by weight, or 35 to 45% by weight. In the block copolymer according to the embodiment, based on the total weight of the block copolymer, poly(aminoester) or the unit represented by Formula 2 as a hydrophobic second block may be contained in an amount of 1 to 99% by weight, 10 to 90% by weight, or 40 to 80% by weight, and may be specifically contained in an amount of 40 to 75% by weight, 45 to 80% by weight, 45 to 75% by weight, 45 to 70% by weight, 50 to 75% by weight, 50 to 70% by weight, 50 to

[Formula 7]

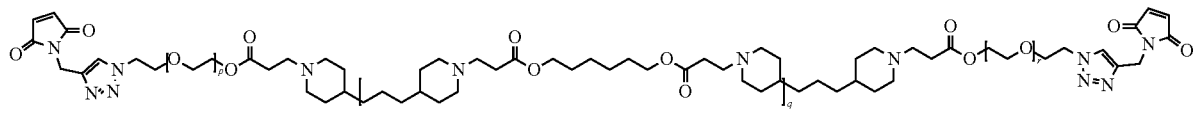

65% by weight, 55 to 70% by weight, or 55 to 65% by weight. In addition, in the block copolymer according to the embodiment, based on the total weight of the block copolymer, as a functional group capable of specifically binding to thiol, a disulfide group, a maleimide group, an alkenyl group, or an alkynyl group may be contained in an amount of 0.01 to 10% by weight, or 0.01 to 5% by weight, and may be specifically contained in an amount of 0.05 to 5% by weight, 0.1 to 5% by weight, 0.5 to 5% by weight, or 1 to 4% by weight.

In addition, in the hydrophilic first block contained in the block copolymer according to the embodiment of the present invention, based on the total weight of the hydrophilic first block, poly(ether) or the unit represented by Formula 1 may be contained in an amount of 10 to 100% by weight, and may be specifically contained in an amount of 30 to 100% by weight, 50 to 100% by weight, 60 to 100% by weight, 70 to 100% by weight, 80 to 100% by weight, or 90 to 100% by weight.

On the other hand, in the hydrophobic second block contained in the block copolymer according to the embodiment of the present invention, based on the total weight of the hydrophobic second block, the poly(aminoester) or the unit represented by Formula 2 may be contained in an amount of 10 to 100% by weight, and may be specifically contained in an amount of 30 to 100% by weight, 50 to 100% by weight, 60 to 100% by weight, 70 to 100% by weight, 80 to 100% by weight, or 90 to 100% by weight.

Meanwhile, in the block copolymer according to the embodiment of the present invention, a ratio of the total weight of the hydrophilic first block to the total weight of the hydrophobic second block may be (1:20) to (20:1), and may be specifically (1:10) to (10:1), (1:10) to (5:1), (1:5) to (5:1), (1:5) to (3:1), (1:5) to (2:1), or (1:5) to (1:1).

In addition, the block copolymer according to an embodiment of the present invention may be a double block copolymer that includes one hydrophilic block and one hydrophobic block, or may be a triple, quadruple, or pentagonal block copolymer that includes two or more hydrophilic blocks or hydrophobic blocks. For example, the block copolymer may have a structure of hydrophilic first block-hydrophobic second block, or have a structure of hydrophilic first block-hydrophobic second block-hydrophilic first block or a structure of hydrophobic second block-hydrophilic first block-hydrophobic second block.

On the other hand, in the block copolymer according to the embodiment of the present invention, the functional group capable of specifically binding to thiol may be connected, directly or via a linker, to the block copolymer's main chain, side chain, or end, or a combination thereof Specifically, the functional group capable of specifically binding to thiol may be connected, via a linker, to the block copolymer's end, for example, an ether group of poly(ether) as a hydrophilic first block, or an amine or ester group of poly(aminoester) as a hydrophobic second block.

The block copolymer according to the embodiment of the present invention may have a total molecular weight of 1,000 to 50,000 Da, and may specifically have a total molecular weight of 2,000 to 45,000 Da, 3,000 to 40,000 Da, 4,000 to 30,000 Da, or 5,000 to 20,000 Da.

In another aspect of the present invention, there is provided a nanoparticle, comprising the above-described block copolymer.

In an embodiment of the present invention, the block copolymer may form a nanoparticle having a micellar structure through self-assembly of the hydrophobic block, and includes both a hydrophilic block and a hydrophobic block so that the hydrophobic block can self-assemble to form a nucleus in a subject or in water, while the hydrophilic block can form the surface that is in contact with water. The micelle is an aggregate of molecules that are collected at a certain concentration or higher, and may mean a structural body in which amphiphilic molecules are aggregated in uniform size and shape. The nanoparticles or micelles may have various shapes such as sphere, ellipsoid, cylinder, ring, and lamella.

In addition, in yet another aspect of the present invention, there is provided a drug delivery vehicle, comprising the above-described nanoparticle and a drug. The nanoparticle may have a micellar structure formed of a block copolymer, and may carry a hydrophobic drug in a nucleus of micelles formed by aggregation of hydrophobic blocks.

The drug delivery vehicle may have an average particle diameter of 50 to 1,000 nm, and more specifically, may have an average particle diameter of 100 to 200 nm. However, the present invention is not limited thereto. As an example, in a case where doxorubicin is contained in the drug delivery vehicle, the drug delivery vehicle may have an average particle size of 20 to 400 nm at a neutral pH, and more specifically, may have an average particle size of 100 to 200 nm. However, the present invention is not limited thereto. The drug delivery vehicles having the corresponding range of average particle diameter may be easily attached to the cell surface without break-down or degradation of their nanoparticle structure or micellar structure while being administered into a subject and flowed through the bloodstream.

Here, the drug is not limited as long as it has hydrophilic/hydrophobic properties enough to be carried on the inner core of a nanoparticle including the above-described block copolymer. Such a drug may be hydrophobic or weakly hydrophilic, and may, for example, have solubility in water at room temperature of 20 mg/mL or less. Here, the drug may be selected from, but is not limited to, anti-cancer agents, anti-proliferative or chemotherapeutic drugs, analgesic agents, anti-inflammatory agents, antiparasitic agents, antiarrhythmic agents, antibacterial agents, antiviral agents, anticoagulants, antidepressants, antidiabetics, antiepileptic agents, antifungal agents, antigout agents, antihypertensives, antimalarials, antimigraines, anti-muscarinic agents, antineoplastic agents, anti-erectile dysfunction agents, immunosuppressants, antiprotozoals, anti-thyroid agents, anti-anxiety agents, sedatives, hypnotics, neuroleptics, β-blockers, cardiotonic agents, corticosteroids, diuretics, anti-Parkinson's disease agents, gastrointestinal agents, histamine receptor antagonists, keratolytic agents, lipid modulators, angina pectoris drugs, Cox-2 inhibitors, leukotriene inhibitors, macrolides, muscle relaxants, nutrients, narcotic analgesics, protease inhibitors, sex hormones, stimulants, muscle relaxants, anti-osmotic agents, anti-obesity drugs, cognitive enhancers, urinary incontinence drugs, benign prostatic drugs, essential fatty acids, non-essential fatty acids, and combinations thereof As an example, the drug may be a hydrophobic or weakly hydrophilic anti-cancer drug, and may include doxorubicin, cisplatin, etoposide, paclitaxel, docetaxel, camptothecin, podophyllotoxin, cyclophosphamide, actinomycin, methotrexate, thalidomide, erlotinib, gefitinib, camptothecin, tamoxifen, anastrozole, flutamide, zoledronate, vincristine, retinoic acid, chlorambucil, vinblastin, prednisone, Testosterone, ibuprofen, naproxen, indomethacin, phenylbutazone, dexamethasone, celecoxib, valdecoxib, nimesulide, corticosteroid, or combinations thereof The drug delivery vehicle may include a non-naturally occurring carrier. In addition, the drug delivery vehicle may further include a bioactive substance, thereby exhibiting a higher effect in treating diseases associated with cancer. Such a bioactive substance means a substance used for treatment, healing, prevention, diagnosis, or the like of diseases, and examples thereof may include cells, proteins or peptides such as growth factors and hormones, nucleic acids, extracellular matrix substances, and drugs having a medicinal therapeutic function.

Examples of a drug as the bioactive substance carried on the drug delivery vehicle may include antibiotics, anti-inflammatory agents, antiviral agents, and antibacterial agents. The antibiotics may be exemplified by antibiotics selected from derivatives and mixtures of tetracycline, minocycline, doxycycline, ofloxacin, levofloxacin, ciprofloxacin, clarithromycin, erythromycin, cefaclor, cefotaxime, imipenem, penicillin, gentamicin, streptomycin, vancomycin, and the like. The anti-inflammatory agent may be exemplified by an anti-inflammatory agent selected from derivatives and mixtures of indomethacin, ibuprofen, ketoprofen, piroxicam, flurbiprofen, diclofenac, and the like. The antiviral agent may be exemplified by an antiviral agent selected from derivatives and mixtures of acyclovir, robavin, and the like. The antibacterial agent may be exemplified by an antibacterial agent selected from derivatives and mixtures of ketoconazole, itraconazole, fluconazole, amphotericin-B, griseofulvin, and the like.

In addition, the protein or peptide that can be carried on or bound to the drug delivery vehicle and delivered into a living body may be exemplified by various bioactive peptides such as hormones, cytokines, enzymes, antibodies, growth factors, transcriptional regulatory factors, blood factors, vaccines, structural proteins, ligand proteins, polysaccharides and receptors, cell surface antigens, and receptor antagonists, which are used for the purpose of treating or preventing diseases, and derivatives and analogs thereof Specifically, the protein or peptide may be exemplified by bone growth factor, liver growth hormone, growth hormone releasing hormones and peptides, interferons and interferon receptors (for example, interferon-alpha, -beta, and -gamma, soluble type I interferon receptors, and the like), granulocyte colony stimulating factors (G-CSFs), granulocyte-macrophage colony stimulating factors (GM-CSFs), glucacon-like peptides (GLP-1 and the like), G-protein-coupled receptors, interleukins (for example, interleukin-1, -2, -3, -4, -5, -6, -7, -8, -9, and the like) and interleukin receptors (for example, IL-1 receptor, IL-4 receptor, and the like), enzymes (for example, glucocerebrosidase, iduronate-2-sulfatase, alpha-galactosidase-A, agalsidase-alpha and -beta, alpha-L-iduronidase, chitinase, butyrylcholinesterase, lipase, glutamate decarboxylase, imiglucerase, uricase, platelet-activating factor acetylhydrolase, neutral endopeptidase, myeloperoxidase, and the like), interleukin and cytokine binding proteins (for example, IL-18bp, TNF-binding protein, and the like), macrophage activators, macrophage peptides, B cell factors, T cell factors, Protein A, allergic inhibitors, tumor necrosis factor (TNF) alpha inhibitors, cell necrosis glycoproteins, immunotoxins, lymphotoxins, tumor necrosis factors, tumor suppressors, metastasis growth factors, alpha-1 antitrypsins, albumin, alpha-lactalbumin, apolipoprotein-E, erythropoietin, high glycated erythropoietin, angiopoietins, hemoglobin, thrombin, thrombin receptor activation peptides, thrombomodulin, blood factors, blood factor a, blood factor XIII, plasminogen activator, fibrin-binding peptides, urokinase, streptokinase, hirudin, Protein C, C-reactive proteins, renin inhibitors, collagenase inhibitors, superoxide dismutase, leptin, platelet derived growth factors, epithelial growth factors, epidermal growth factors, angiostatin, angiotensin, osteogenic growth factors, bonemorphogenetic proteins, calcitonin, insulin, atriopeptin, cartilage inducers, elcatonin, connective tissue activators, tissue factor pathway inhibitors, follicle stimulating hormones, lutein formation hormones, luteinizing hormone-releasing hormones, nerve growth factors (for example, nerve growth factor, ciliary neurotrophic factor, axogenesis factor-1, brain-natriuretic peptide, glial derived neurotrophic factor, netrin, neutrophil inhibitor factor, neurotrophic factor, and neurturin), parathyroid hormones, relaxin, secretin, somatomedin, insulin-like growth factor, adrenocortical hormones, glucagon, cholecystokinin, pancreatic polypeptides, gastrin releasing peptides, corticotropin releasing factors, thyroid stimulating hormones, autotaxin, lactoferrin, myostatin, receptors (for example, TNFR (P75), TNFR (P55), IL-1 receptor, VEGF receptor, B cell activator receptor, and the like), receptor antagonists (for example, IL1-Ra), cell surface antigens (for example, CD 2, 3, 4, 5, 7, 11a, 11b, 18, 19, 20, 23, 25, 33, 38, 40, 45, 69), monoclonal antibodies, polyclonal antibodies, antibody fragments (for example, scFv, Fab, Fab', F(ab')2, and Fd), and virus-derived vaccine antigens.

The nucleic acid that can be physically carried on or chemically bound to the drug delivery vehicle and delivered into a living body may be exemplified by DNA, RNA, PNA, and an oligonucleotide.

The cell that can be physically carried, together with a bioactive substance, on the drug delivery vehicle and delivered into a living body may be exemplified by stem cells, fibroblasts, vascular endothelial cells, smooth muscle cells, neurons, chondrocytes, osteocytes, skin cells, and Schwann cells.

The drug delivery vehicle according to the embodiment of the present invention may have an average diameter of 25 to 400 nm, or 50 to 200 nm. For example, in a case where a drug delivery vehicle is formed by causing doxorubicin as a drug to be carried on a nanoparticle including the block copolymer represented by Formula 4 or 5, the nanoparticles may have an average diameter of 100 to 200 nm, and an inclusion rate of doxorubicin may be as high as 5 to 10% by weight based on the total weight of the nanoparticle.

An exemplary action of the drug delivery vehicle according to the embodiment of the present invention will be described in more detail with reference to FIG. 1. As illustrated in FIG. 1, a drug delivery vehicle (in the form of micelle) including a block copolymer of an embodiment, on which an anti-cancer drug is carried, is attached to the surface of a natural killer cell that is an immune cell, via a functional group (not shown) capable of specifically binding to a thiol group which is included in the block copolymer, so that the immune cell is potentiated; and in a case where the potentiated immune cells recognize and begin to attack cancer cells, their surrounding environment becomes acidic and causes the drug delivery vehicle to undergo a structural change so that the anti-cancer drug carried on the micelle can be released to induce death of the cancer cells.

As such, the drug delivery vehicle according to the embodiment of the present invention can accurately deliver a highly toxic anti-cancer drug near cancer cells, which makes it possible to utilize a chemical anti-cancer drug that has a large anti-cancer effect but has limitations due to a big side effect caused by its non-specific toxicity, and also allows an effect of maximizing anti-cancer therapeutic efficiency and capacity to be exerted. In addition, while the drug delivery vehicle according to the embodiment is attached to an immune cell and flows through the bloodstream, drug release is suppressed due to its surrounding neutral environment, which makes it possible to avoid systemic toxicity caused by its carried-on anti-cancer drug.

In still yet another aspect of the present invention, there is provided a modified cell obtained by causing a drug delivery vehicle that includes the above-described block copolymer and a drug to be bound to the surface of an immune cell. The modified cell may further include the non-naturally occurring carrier and/or the bioactive substance as described above.

In addition, the immune cell may be selected from, for example, T cells, natural killer cells, dendritic cells (DCs), macrophages, microglial cells, and combinations thereof In addition, the immune cell may include a thiol group on the surface thereof, and thus may have a potentiated effect in a case of being bound to the block copolymer of the embodiment, with such binding made via a functional group capable of specifically binding to a thiol group which is included in the block copolymer. Specifically, like T cells and natural killer cells, the immune cell may form an immune synapse and release lytic granules to perform a cell-killing action. In addition, the immune cell may have a feature of being acidified near the immune synapse while attacking cancer cells. Due to this feature of the immune cell, in response to the acidic environment around cancer cells, the hydrophobic second block of the block copolymer of the embodiment may be decomposed or become cationic so that a drug carried on the block copolymer is released.

In still yet another aspect of the present invention, there is provided a pharmaceutical composition for anticancer use, comprising the above-described block copolymer and an anti-cancer drug. In addition, in still yet another aspect of the present invention, there is provided a pharmaceutical composition for anticancer use or for preventing or treating infection, comprising the above-described block copolymer, a drug, and an immune cell.

The cancer may be selected from colon cancer, lung cancer, non-small cell lung cancer, bone cancer, pancreatic cancer, skin cancer, head cancer, cervical cancer, skin melanoma, intraocular melanoma, uterine cancer, ovarian cancer, rectal cancer, gastric cancer, perianal cancer, breast cancer, fallopian tube carcinoma, endometrial carcinoma, cervical carcinoma, vaginal carcinoma, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penis cancer, prostate cancer, chronic leukemia, acute leukemia, lymphocyte lymphoma, bladder cancer, kidney cancer, ureteral cancer, renal cell carcinoma, renal pelvic carcinoma, and central nervous system (CNS) tumor. However, the cancer is not particularly limited thereto.

In an embodiment of the present invention, the pharmaceutical composition means a composition that is administered for a specific purpose. For the purposes of the present invention, the pharmaceutical compositions of the present invention may be used for the purpose of preventing or treating a cancer disease or disorder, or infection, and may include a protein involved therein and a pharmaceutically acceptable carrier, excipient, or diluent. In addition, the pharmaceutical composition of the present invention may further include the non-naturally occurring carrier and/or the bioactive substance as described above.

The pharmaceutically acceptable carriers or excipients are those approved by the government's regulatory department, or those listed in the government-approved pharmacopeia or other generally recognized pharmacopeias for use in vertebrates, and more particularly in humans.

To be suitable for parenteral administration, the pharmaceutical composition may be prepared in the form of a suspension, solution, or emulsion which has an oily or aqueous carrier, may be prepared in the form of a solid or semisolid, and may include a formulating agent such as suspending agent, stabilizer, solubilizer, and/or dispersant. This form may be sterile and may be liquid. The pharmaceutical composition may be stable under preparation and storage conditions and may be preserved against contaminating action of microorganisms such as bacteria or fungi. Alternatively, the pharmaceutical composition may be in sterile powder form for reconstitution with a suitable carrier prior to use. The pharmaceutical composition may be in unit-dose form, in microneedle patches, in ampoules, or in other unit-dose containers or in multi-dose containers. Alternatively, the pharmaceutical composition may be stored in a lyophilized (freeze-dried) state that requires only addition of a sterile liquid carrier, for example, water for injection immediately prior to use. Extemporaneous injection solutions and suspensions may be prepared with sterile powders, granules, or tablets.

In some non-limiting embodiments, the pharmaceutical composition of the present invention may be formulated into liquids or included, in a liquid, in the form of microspheres. In certain non-limiting embodiments, the pharmaceutical composition of the present invention includes a pharmaceutically acceptable compound and/or mixture at a concentration of 0.001 to 100,000 U/kg. In addition, in certain non-limiting embodiments, an excipient suitable for the pharmaceutical composition of the present invention includes preservatives, suspending agents, stabilizers, dyes, buffers, antibacterial agents, antifungal agents, and isotonic agents, such as sugar or sodium chloride. The stabilizer refers to a compound optionally used in the pharmaceutical composition of the present invention in order to increase storage life thereof In a non-limiting implementation, the stabilizer may be a sugar, an amino acid, a compound, or a polymer. The pharmaceutical composition may include one or more pharmaceutically acceptable carriers. The carrier may be a solvent or a dispersion medium. Non-limiting examples of the pharmaceutically acceptable carrier include water, saline, ethanol, polyol (for example, glycerol, propylene glycol, and liquid polyethylene glycol), oil, and suitable mixtures thereof In addition, parenteral formulations may be sterilized. Non-limiting examples of sterilization techniques include filtration through a bacterial-retaining filter, terminal sterilization, incorporation of sterile preparations, radiation sterilization, sterile gas irradiation, heating, vacuum drying, and lyophilization.

In an embodiment of the present invention, the term "administration" means introducing the composition of the present invention into a patient by any suitable method. The composition of the present invention may be administered through any general route as long as the route allows the composition of the present invention to reach a target tissue. The composition of the present invention may be administered orally, intraperitoneally, intravenously, intramuscularly, subcutaneously, intradermally, intranasally, intrapulmonarily, intrarectally, intracavitarily, or intrathecally. However, in a case of the pharmaceutical composition, which includes the drug delivery vehicle according to the present invention, since the drug delivery vehicle has to be attached to cells so that both chemotherapy and immunotherapy are performed, the pharmaceutical composition is preferably administered parenterally and may be administered in the form of injectables.

In still yet another aspect of the present invention, there is provided a method for preventing or treating a cancer disease or disorder, comprising administering, to a subject, the above-described block copolymer and an anti-cancer drug. The prevention or treatment method may be performed by simultaneously administering, to the subject, pharmaceutical compositions including the above-described block copolymer and a drug in pharmaceutically effective amounts. Alternatively, the prevention or treatment method may be performed by administering, to the subject, the block copolymer and the drug at a time interval.

In still yet another aspect of the present invention, there is provided a method for preventing or treating a cancer disease or disorder, or infection, comprising administering the above-described block copolymer, a drug, and an immune cell. The prevention or treatment method may comprise simultaneously administering, to a subject, pharmaceutical compositions including the above-described block copolymer, a drug, and an immune cell in pharmaceutically effective amounts. Alternatively, the prevention or treatment method may be performed by administering, to the subject, the block copolymer, the drug, and the immune cell at a time interval.

In the present invention, an effective amount may be regulated depending on various factors, including type of cancer disease, severity of disease, types and amounts of active ingredient and other ingredients contained in the composition, type of formulation and the patient's age, weight, general health condition, sex and diet, time of administration, route of administration and secretion rate of the composition, duration of treatment, and simultaneously used drugs.

In the present invention, the term "subject" may mean a human, and a mammal including a cow, a horse, a sheep, a pig, a goat, a camel, an antelope, a dog, or the like, and may mean a mammal except a human.

On the other hand, in still yet another aspect of the present invention, there is provided a method for preparing the above-described block copolymer.

The method for preparing the block copolymer may comprise the steps of: S1) reacting a hydrophilic polymer that includes a hydrophilic first block with a hydrophobic polymer that includes a hydrophobic second block; and S2) reacting the hydrophilic polymer or the hydrophobic polymer with a compound that includes a functional group capable of specifically binding a thiol group. The respective steps of the preparation method may be changed in terms of their order.

The step S1 may be performed by comprising a step of introducing a first inducing functional group into one of the hydrophilic polymer and the hydrophobic polymer; and a step of reacting one of the hydrophilic polymer and the hydrophobic polymer, into which the first inducing functional group is introduced, with the other of the hydrophobic polymer and the hydrophilic polymer.

In addition, the step S2 may be performed by comprising a step of introducing a second inducing functional group into one of the hydrophilic polymer and the hydrophobic polymer; and a step of reacting one of the hydrophilic polymer and the hydrophobic polymer, into which the second inducing functional group is introduced, with a compound that includes a functional group capable of specifically binding to a thiol group. Here, the step of introducing the second inducing functional group may be performed before the step S1. In addition, the step S2 may further include a step of introducing a third inducing functional group to the compound that includes a functional group capable of specifically binding to a thiol group.

Specifically, the method for preparing a block copolymer according to the embodiment may comprise the steps of: S1-1) introducing a first inducing functional group and a second inducing functional group to a hydrophilic polymer that includes a hydrophilic first block; S1-2) reacting the hydrophilic polymer, which includes the first inducing functional group and the second inducing functional group, with a hydrophobic polymer that includes a hydrophobic second block, wherein the reaction occurs through the first inducing functional group; S2-1) introducing a third inducing functional group into a compound that includes a functional group capable of specifically binding to a thiol group; and S2-2) reacting the hydrophilic polymer, the hydrophobic polymer, or a combination thereof with the compound that includes a functional group capable of specifically binding a thiol group, into which the third inducing functional group is introduced, wherein the reaction occurs through the third inducing functional group. The respective steps of the preparation method may be changed in terms of their order. For example, the step S2-1 may be performed before the step S1-1.

The hydrophilic polymer means a polymer that includes the above-described hydrophilic first block and is hydrophilic. A number average molecular weight (Mn) of the hydrophilic polymer is not particularly limited, and may be 500 to 5,000 g/mol, specifically 1,000 to 3,000 g/mol, or 1,500 to 2,500 g/mol. In a case where the number average molecular weight of the hydrophilic polymer is less than 500 g/mol or more than 5,000 g/mol, it may be difficult for the hydrophilic polymer to form a micelle through self-assembly caused by hydrophilic/hydrophobic balance at a specific pH condition; or even if a micelle is formed, the micelle may break down by being dissolved in water or may alternatively precipitate. The hydrophilic polymer may be, for example, a polyethylene glycol-based polymer.

The hydrophobic polymer means a polymer that includes the above-described hydrophobic second block and is hydrophobic. The number average molecular weight (Mn) of the hydrophobic polymer is likewise not particularly limited, and may be 1,500 to 27,000 g/mol, 3,000 to 13,000 g/mol, 3,000 to 10,000 g/mol, or 4,500 to 8,500 g/mol. The hydrophobic polymer may be, for example, poly(aminoester), poly(amidoamine), or poly(aminoester)(amidoamine) Since these polymers have a property that their solubility in water varies depending on pH conditions due to an amine group present therein, a micellar structure may be formed or may break down depending on changes in pH condition. The hydrophobic polymer may be prepared according to a method commonly known in the art, and may be obtained, for example, by performing polymerization of a bisacrylate compound or a bisacrylamide compound with an amine-based compound through a Michael reaction.

The compound that includes a functional group capable of specifically binding to a thiol group means a compound including the above-described functional group capable of specifically binding to a thiol group. Specifically, the compound that includes a functional group capable of specifically binding to a thiol group may be disulfide, maleimide, alkene, alkyne, or the like. More specifically, the compound may be maleimide or maleimide alkyne, but is not particularly limited thereto.

The first inducing functional group means a functional group for introduction into a hydrophilic polymer or a hydrophobic polymer so that the hydrophilic polymer and the hydrophobic polymer are connected to each other, and this first inducing functional group may be appropriately selected depending on the type of a functional group present in the hydrophilic polymer or the hydrophobic polymer. For example, in a case where the hydrophilic polymer includes a hydroxyl group and the hydrophobic polymer includes an amine group, an alkenyl group, an alkynyl group, or an acrylate group as the first inducing functional group may be introduced at the hydroxyl group position of the hydrophilic polymer so that the first inducing functional group can react with the amine group of the hydrophobic polymer, wherein such a first inducing functional group enables connection/copolymerization of the hydrophilic polymer and the hydrophobic polymer by radical polymerization. In addition, in consideration of selection of solvent, polymerization temperature, and the like, the first inducing functional group such as an alkenyl group, an alkynyl group, or an acrylate group may be easily introduced into the hydrophilic polymer out of the hydrophilic polymer and the hydrophobic polymer.

The second inducing functional group means a functional group for introduction into a hydrophilic polymer or a hydrophobic polymer so that the hydrophilic polymer or the hydrophobic polymer is connected to the compound that includes a functional group capable of specifically binding to a thiol group, and this second inducing functional group may be appropriately selected depending on the type of a functional group present in the hydrophilic polymer or the hydrophobic polymer and the type of the functional group capable of specifically binding to a thiol group. For example, in a case where the hydrophilic polymer includes a hydroxyl group, an azide group as the second inducing functional group may be introduced at the hydroxyl group position of the hydrophilic polymer.

The third inducing functional group means a functional group for introduction into the compound that includes a functional group capable of specifically binding to a thiol group so that the hydrophilic polymer or the hydrophobic polymer is connected to the compound that includes a functional group capable of specifically binding to a thiol group, and this third inducing functional group may be appropriately selected depending on the type of a functional group present in the hydrophilic polymer or the hydrophobic polymer and the type of the functional group capable of specifically binding to a thiol group. For example, in a case where an azide group is present in the hydrophilic polymer or the hydrophobic polymer, an alkenyl group, an alkynyl group, an acrylate group, or a disulfide group as the third inducing functional group may be introduced into the compound that includes a functional group capable of specifically binding to a thiol group. Among these, the alkenyl group and the azide group have advantages that reaction can be easily allowed to proceed through a simple process due to their very simple reaction condition such as reaction being carried out through click chemistry. However, the present invention is not particularly limited thereto.

In the step S1, a reaction weight ratio of the hydrophilic polymer to the hydrophobic polymer may be (1:20) to (20:1), specifically (1:10) to (10:1), (1:10) to (5:1), (1:5) to (5:1), (1:5) to (3:1), (1:5) to (2:1), or (1:5) to (1:1). In a case where the reaction weight ratio is not within the range, too little hydrophobic blocks in the final block copolymer may prevent a micelle from forming and may cause the hydrophilic polymer and the hydrophobic polymer to be present in a dissolved state, or too many hydrophobic blocks may prevent a micelle from forming and may cause the hydrophilic polymer and the hydrophobic polymer to precipitate.

In addition, a reaction molar ratio of the hydrophilic polymer to the hydrophobic polymer may be (1:5) to (5:1), specifically, (1:4) to (4:1), (1:3) to (3:1), (1:2) to (3:1), or (1:1) to (3:1). By regulating the reaction molar ratio, it is possible to form various block forms including a double block copolymer, a triple block copolymer or a higher-order block copolymer.

A molecular weight range of the copolymer prepared according to the preparation method is not particularly limited, and may be 1,000 to 50,000 g/mol and specifically, 2,000 to 45,000 g/mol, 3,000 to 40,000 g/mol, 4,000 to 30,000 g/mol, or 5,000 to 20,000 g/mol. In a case where the molecular weight is less than 1,000 g/mol, it is not only difficult for the block copolymer to form a micelle at a specific pH, but also even if a micelle is formed, the micelle is dissolved in water and easily breaks down. In addition, in a case where the molecular weight exceeds 50,000 g/mol, due to collapse of hydrophilic/hydrophobic balance, a micelle may not be formed and may precipitate at a specific pH.

Meanwhile, in still yet another embodiment of the present invention, there is provided a method for preparing a nanoparticle that includes the above-described block copolymer, comprising a step of preparing the block copolymer; and a step of mixing the block copolymer, a solvent, and an aqueous solution to form a nanoparticle. For example, the nanoparticle forming step may be performed by first mixing the block copolymer and the solvent and then causing the mixture to be mixed with the aqueous solution so that a micelle is formed.

For the solvent, toluene, chloroform, tetrahydrofuran, dimethyl sulfoxide, dimethyl formamide, methylene chloride, or the like may be used. In addition, in the micelle forming step, methods such as stirring, heating, ultrasonic scanning, solvent evaporation using emulsification, matrix formation, or dialysis using an organic solvent may be used alone or in combination.

In still yet another embodiment of the present invention, there is provided a method for preparing a drug delivery vehicle that includes the above-described block copolymer and a drug, comprising: a step of preparing the block copolymer; and a step of mixing the block copolymer and the drug to form a drug delivery vehicle. For example, the drug delivery vehicle forming step may be performed by first mixing the block copolymer, the drug, and a solvent to prepare a mixture, and then adding an aqueous solution to the mixture to form a micelle. The solvent and the micelle forming method are as described above.

In addition, in still yet another embodiment of the present invention, there is provided a method for producing a modified cell that includes the above-described drug delivery vehicle and an immune cell, comprising: a step of preparing the above-described block copolymer; and a step of mixing the block copolymer, a drug, and an immune cell to form a modified cell. For example, the modified cell forming step may be performed by forming a nanoparticle that includes the block copolymer and the drug, and then causing the nanoparticle to be mixed with the immune cell. The modified cell may be formed by binding of a thiol group present on the surface of the immune cell with a functional group specifically binding to thiol exposed on the surface of the nanoparticle. The solvent and the nanoparticle forming method are as described above.

Mode for the Invention

Hereinafter, preferred examples are provided to help understanding of the present invention. However, it is apparent to those skilled in the art that the following examples are merely to illustrate the present invention and that various changes and modifications can be made within the scope and spirit of the present invention; and it is also obvious that such changes and modifications belong to the appended claims.

EXAMPLE 1

Synthesis of Block Copolymer and Drug Delivery Vehicle, and Characteristic Evaluation thereof

EXAMPLE 1.1

Figure 2:
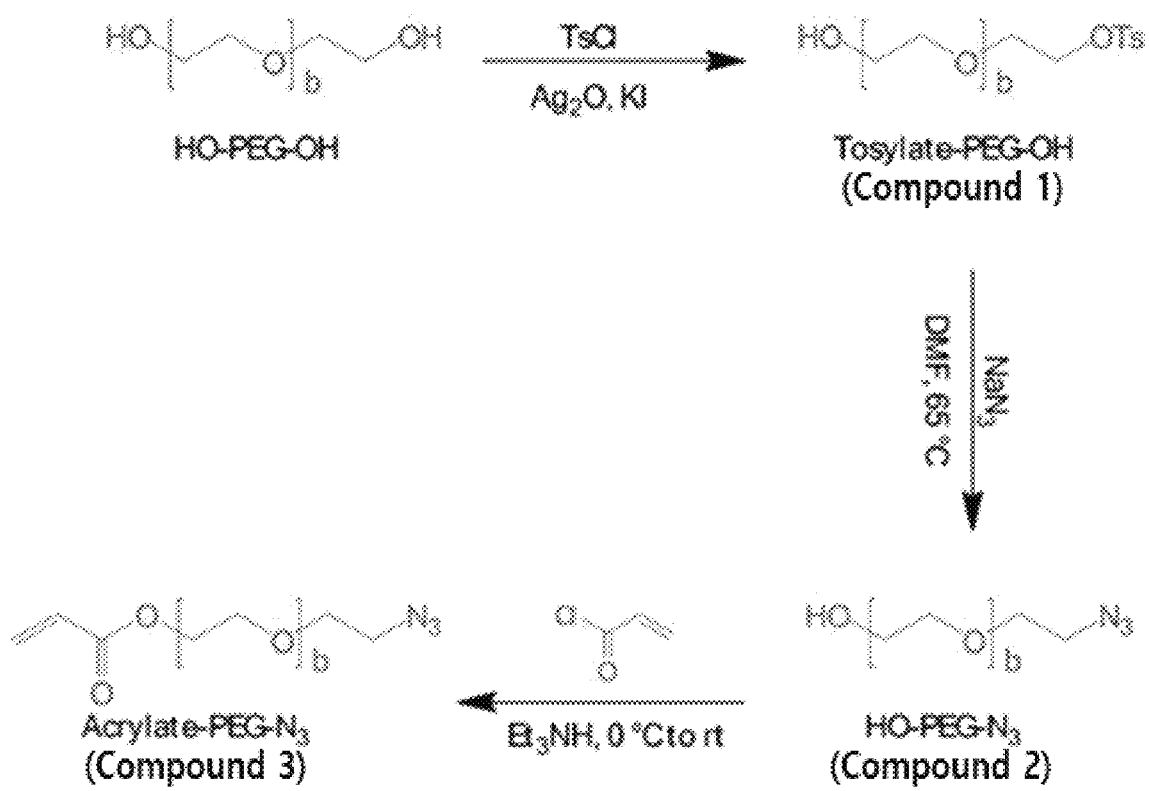
FIG. 2 illustrates a reaction scheme for synthesizing a hydrophilic first block in the block copolymer according to the embodiment of the present invention.

Synthesis of Hydrophilic Polymer including Hydrophilic First Block in Block Copolymer To synthesize a block copolymer that includes a hydrophilic first block, a hydrophobic second block, and a functional group capable of specifically binding to thiol, acrylate-PEG-N3, which serves as a hydrophilic polymer including a hydrophilic block, was first synthesized in the same manner as in FIG. 2. First of all, PEG (10.000 g; 5 0 mmol) having a molecular weight of 2,000 Da was dissolved in 160 mL of cold $CH_2Cl_2$, and then $Ag_2O$ (1.738 g; 7.5 mmol), KI (0.332 g; 2 0 mmol), and TsCl (1 g; 5.25 mmol) dissolved in 20 mL of $CH_2Cl_2$ were added with vigorous stirring. This reaction was allowed to proceed under nitrogen atmosphere for 2 hours and the reaction product was filtered off by silica gel. The solvent was removed from the reaction product and then recrystallized to obtain pure tosylate-PEG-OH (Compound 1). A yield of this reaction was determined to be 81%. Subsequently, $NaN_3$ (0.605 g; 9.3 mmol) was added to tosylate-PEG-OH (Compound 1) (4.000 g; 1.86 mmol) under 40 mL of DMF solvent, and stirring was performed at 65° C. for 18 hours. The temperature was lowered to room temperature, and then DMF was removed in vacuo. The resultant was dissolved in $CH_2Cl_2$, and then passed through silica gel to obtain HO-PEG-$N_3$ (Compound 2). A yield of this reaction was determined to be 76%.

Finally, HO-PEG-$N_3$ (Compound 2) (2.0 g, 0.980 mmol) thus obtained was dissolved in 15 mL of cold $CH_2Cl_2$ with TEA (0.397 mL; 3.980 mmol). To this mixture, a solution of acryloyl chloride (0.266 mL; 2.940 mmol) dissolved in 15 mL of $CH_2Cl_2$ was slowly added dropwise under nitrogen atmosphere. After all additions completed, the reaction product was stirred under nitrogen atmosphere for 24 hours so that the reaction product cools slowly to room temperature. The solvent was removed in vacuo, and then the remaining reaction product was dissolved again in THF solvent to remove $Et_3N.HCl$ salt. Then, the resultant was precipitated in diethyl ether to obtain the final product, acrylate-PEG-N3 (Compound 3). A yield of this reaction was determined to be 75%.

Figure 3:
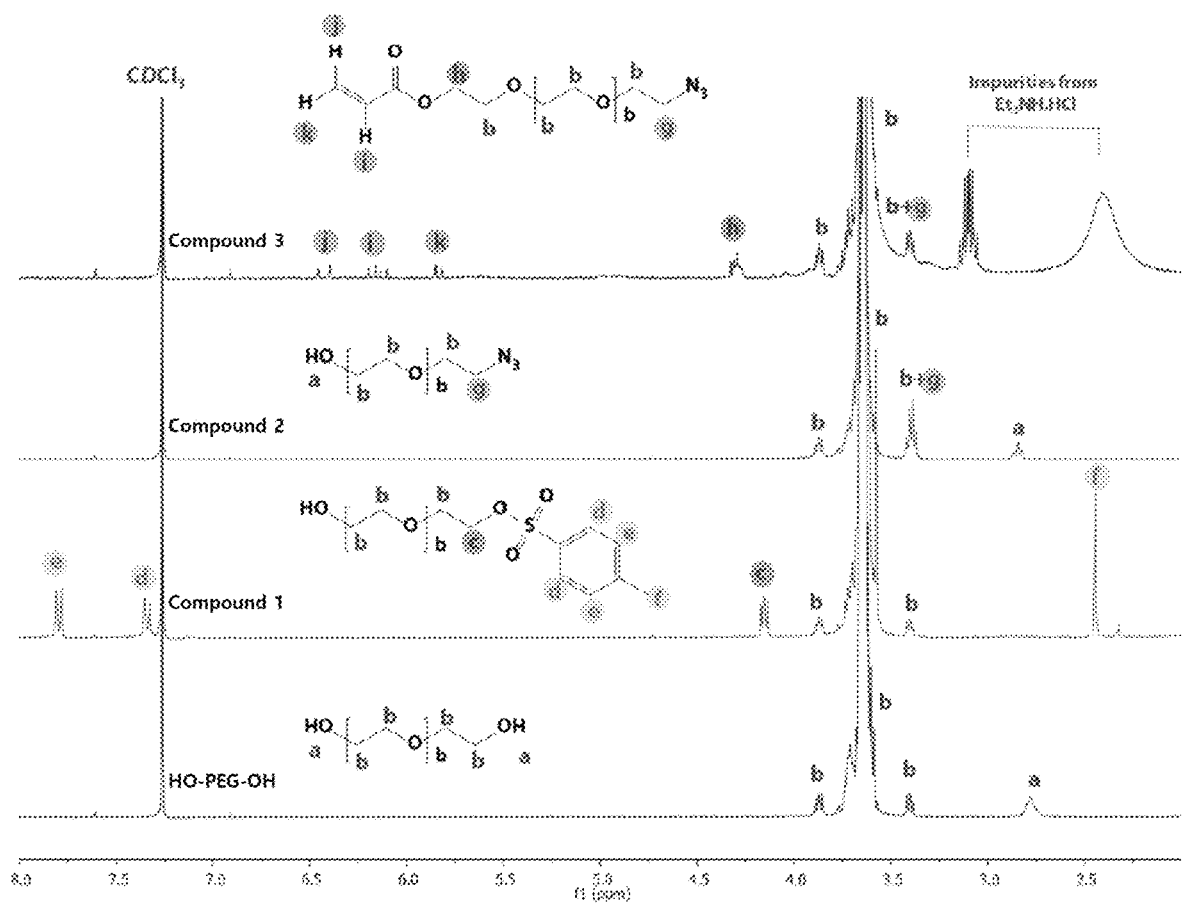
FIG. 3 illustrates 1H-NMR spectra for the intermediate compounds and the final compound in synthesis of the hydrophilic first block in the block copolymer according to the embodiment of the present invention.

The $^1H$ NMR ($CDCl_3$) results for Compounds 1 to 3 are illustrated in FIG. 3.

EXAMPLE 1.2

Figure 4:
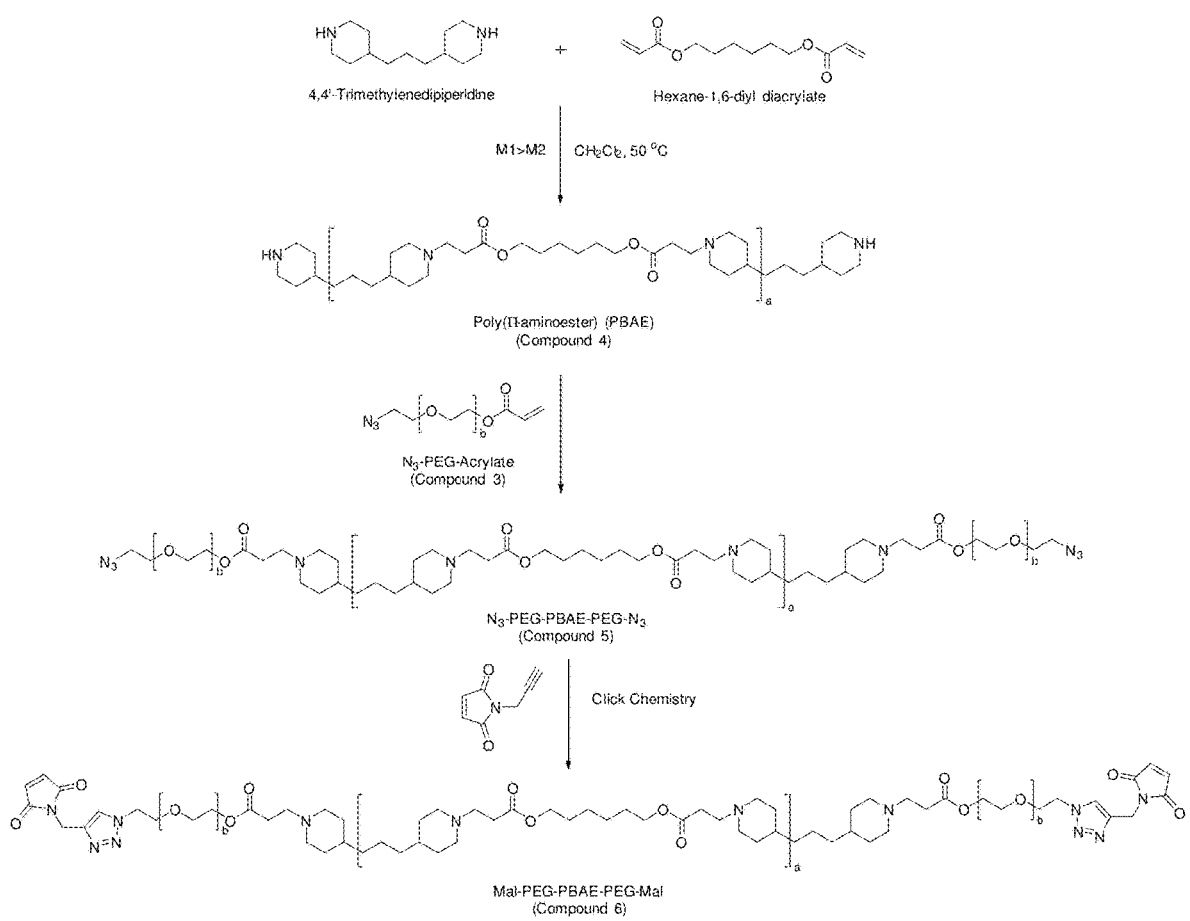
FIG. 4 illustrates a reaction scheme for synthesizing a hydrophobic second block in the block copolymer according to the embodiment of the present invention.

Synthesis of Hydrophobic Polymer including Hydrophobic Second Block in Block Copolymer To continuously synthesize the block copolymer, Mal-PEG-PBAE-PEG-Mal having a molecular weight of 10,000 Da, which serves as a hydrophobic polymer including a hydrophobic second block, was synthesized in the same manner as in FIG. 4.

Figure 5:
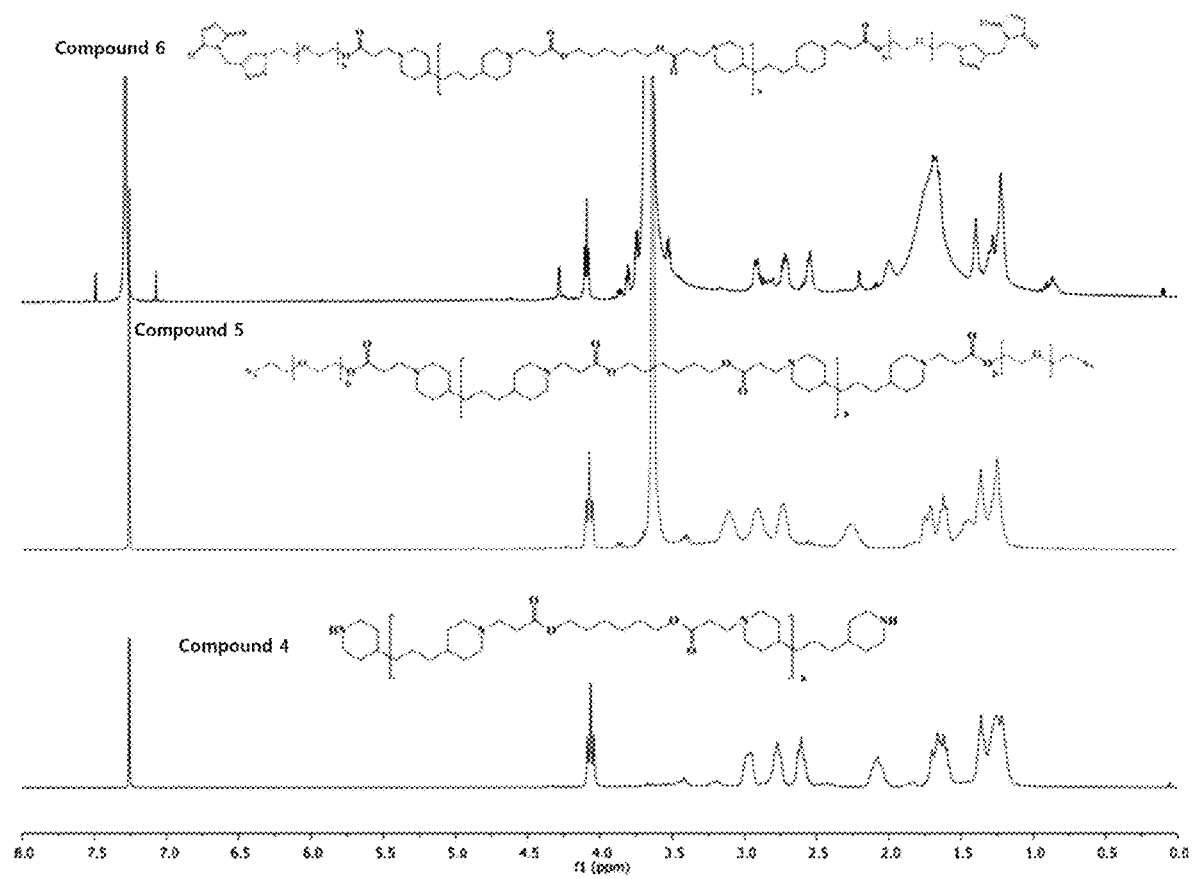
FIG. 5 illustrates 1H-NMR spectra for the intermediate compounds and the final compound in synthesis of the hydrophobic second block in the block copolymer according to the embodiment of the present invention.

First of all, 4,4'-trimethylenedipiperidine (TMDP) (M1, 0.542 g; 2.578 mmol) and hexane-1,6-diyl diacrylate (HDDA) (M2, 0.500 g; 2.210 mmol) were dissolved in 10 mL of anhydrous $CH_2Cl_2$. Then, polymerization was performed at 40° C. for 2 days, from which poly(β-aminoester) (PBAE) (Compound 4) was synthesized. The $^1H$ NMR ($CDCl_3$) result for Compound 4 is illustrated in FIG. 5.

EXAMPLE 1.3

Synthesis of Block Copolymer

Then, acrylate-PEG-N3 (Compound 3) (0.794 g; 0.382 mmol) synthesized in Example 1.1 was dissolved in 2 mL of anhydrous $CH_2Cl_2$ and added to the reaction. The reaction was allowed to proceed at 40° C. for 2 days. As a result, $N_3$-PEG-PBAE-PEG-$N_3$ (Compound 5) was synthesized and purified by precipitation with diethyl ether. A yield of this reaction was determined to be 93%.

Finally, alkyne-maleimide (0.032 g; 0.230 mmol) was attached to $N_3$-PEG-PBAE-PEG-$N_3$ (Compound 5) (0.500 g, 0.045 mmol) through copper-mediated click chemistry. Both reactants were dissolved in 10 mL of DMF with 1-(prop-2-ynyl)-1H-pyrrole-2,5-dione (0.008 g, 0.045 mmol), and reaction was allowed to proceed for 30 minutes under an environment of nitrogen injection. Subsequently, CuBr (0.007 g; 0.045 mmol) was added under nitrogen atmosphere, and click chemistry was allowed to proceed at 45° C. for 24 hours. Then, the resultant was passed through silica gel to remove the copper catalyst and precipitated in diethyl ether to obtain a Mal-PEG-PBAE-PEG-Mal copolymer (Compound 6).

The $^1H$ NMR ($CDCl_3$) results for Compounds 5 and 6 are illustrated in FIG. 5.

EXAMPLE 1.4

Formation of Drug Delivery Vehicle

To form a drug delivery vehicle (ReMi) that includes the block copolymer and a drug, 100 mg of Mal-PEG-PBAE-PEG-Mal copolymer (Compound 6) synthesized in Example 1.3 was dissolved in 4 mL of DMSO, and the anti-cancer drug, doxorubicin (DOX), at a concentration of 50 μg/mL was added thereto. Subsequently, 20 mL of distilled water was added dropwise while vigorously stirring the mixture, and then stirring was performed for another 30 minutes. This solution was dialyzed against distilled water through a dialysis membrane with a size of 3,500 Da. ReMi thus obtained was lyophilized and stored.

EXAMPLE 1.5

Synthesis of Indicator Beads of which Fluorescence Increases as Acidity Increases Amine-modified polystyrene beads (200 nm, 5.68×10$^{11}$ particles) and succinimidyl 3-(2-pyridyldithio)propionate (SPDP) (1.16 mg; 3.7248 !mop were dissolved in 5 mL of DMSO, and then reaction was allowed to proceed, with shaking, at room temperature for 30 minutes. Then, 10 mM tris (2-carboxyethyl)phosphine (TCEP) (1.43 mg; 5 μmol) was added and then stirred at room temperature for 30 minutes. Then, pHrodo-Maleimide phosphor (0.6 mg, 0.65 !mop was added and stirred under a dark condition at room temperature for 1 hour. Then, NHS-PEG-Maleimide (5000 Da; 31.04 mg; 6.208 !mop was added to remove residual amine residues, and reaction was allowed to proceed under a dark condition at room temperature for 24 hours. The thus synthesized beads were centrifuged at 4000 rpm for 2 minutes, and then the supernatant was removed to obtain indicator beads.

EXAMPLE 1.6

Characteristic Analysis of Drug Delivery Vehicle

In order to identify whether the drug delivery vehicle (ReMi) formed in Example 1.4 has stimulus responsiveness depending on pH changes, the average hydration size distribution was calculated with dynamic light scattering (DLS) under conditions of pH 11, pH 7.5, and pH 5.5, and under a condition of pH 7.5 left for 3 days. The results are illustrated in FIG. 6.

As illustrated in FIG. 6, it was identified that ReMi was decomposed only at an acidic condition and thus exhibited a decreased hydration size, and it was identified that ReMi was stable under normal conditions from the viewpoint that its hydration size was maintained even after being left for 3 days. This result was also identified with the transmission electron microscopic images illustrated in FIG. 7.

EXAMPLE 1.7

Characteristic Analysis of Drug Release Control in Drug delivery Vehicle

In order to identify whether the drug delivery vehicle (ReMi) formed in Example 1.4 exhibits changes in drug release behavior depending on pH changes, the drug release behavior of ReMi with pH was checked by measuring fluorescence at characteristic fluorescence wavelengths (ex=495 nm; ex=595 nm) of doxorubicin (DOX). ReMi was administered to the aqueous solution conditions set at pH 7.5 and pH 5.5, respectively, and the fluorescence intensity of DOX emitted through dialysis was measured by a fluorescence photometer. The results are illustrated in FIG. 8. From FIG. 8, it was identified that 70% of the drug was released from ReMi within 48 hours under an acidic environment, and that only around 20% of the drug was released to the outside during the same time under a neutral condition.

EXAMPLE 1.8

Characteristic Analysis of cell Attachment of Drug Delivery Vehicle

In order to identify whether the drug delivery vehicle (ReMi) formed in Example 1.4 can be successfully attached to immune cells, ReMi was incubated with natural killer cells (NK cells), and then the cells were collected after 30 minutes to prepare a microscope sample. The thus prepared microscope sample was observed with a fluorescence microscope. The results are illustrated in FIG. 9.

As illustrated in FIG. 9, it was identified that ReMi was successfully attached to the surface of immune cells.

EXAMPLE 2

Identification on Whether Drug Delivery Vehicle Recognizes and Attacks Cancer Cells in Case of being used The drug delivery vehicle (ReMi) formed in Example 1.4 was attached to the surface of natural killer cells, and then fluorescence microscopic images were taken continuously for 4 hours. The images thereof are illustrated in FIGS. 10 and 11. Here, the surface of the natural killer cells was modified with the indicator beads, of which the fluorescence intensity increased as acidity increases, prepared according to Example 1.5.

As illustrated in FIG. 10, it was identified that in a case where natural killer cells attacked cancer cells, acidity of the surrounding environment of the natural killer cells gradually increased.

As illustrated in FIG. 11, ReMi on which an anti-cancer drug was carried was continuously observed for 4 hours by fluorescence microscopy, and as a result, it was identified through increased fluorescence intensity that the anti-cancer drug, doxorubicin, was released from ReMi as the natural killer cells began to recognize and attacked the cancer cells.

That is, it was identified that in a case where an immune cell recognizes and attacked a cancer cell, acidity around the immune cell increases, which allowed the drug to be released from the drug delivery vehicle.

EXAMPLE 3

Evaluation of Stability of Drug Delivery Vehicle

Stability of the drug delivery vehicle was identified through cytotoxicity assay. 8,000 A549-LUC cells, or 24,000 NK-92MI cells were dispensed in 96-well cell culture plates, and then incubated for 1 day. Subsequently, 20 μL of ReMi carrying 0.3 μM doxorubicin was added to each well and incubated for 12 hours. Then, the cell death was checked through the MTS cytotoxicity assay, and the results are illustrated in FIG. 12.

As illustrated in FIG. 12, it was identified that ReMi itself did not damage cancer cells and natural killer cells.

EXAMPLE 4

Identification of Immune Cell's Anti-Cancer Effect Potentiated by Drug Delivery Vehicle An immune cell's anti-cancer effect potentiated by the drug delivery vehicle was identified through cytotoxicity assay. 8,000 A549-LUC cells were dispensed in 96-well cell culture plates, and then incubated for 1 day. Then, the A549-LUC cells were dispensed at a density of $1 \times 10^3$ cells per well, and each sample was added to each well according to the conditions as shown in Table 1. Incubation was performed for 12 hours. Then, the cell death was checked through the MTS cytotoxicity assay, and the results are illustrated in FIG. 13. Here, the results illustrated in FIG. 13 are a graphical representation obtained by setting the anti-cancer capacity, exerted in a case where doxorubicin and natural killer cells (DOX +NK) are co-administered, as 100% and also setting the anti-cancer capacity, exerted in a case where only treatment with PBS is performed, as 0%. ReMi used was the one carrying 0.3 t.tM doxorubicin, prepared in Example 1.4, and ReNK means natural killer cells to which ReMi is attached.

TABLE 1

| Sample name | Dosage of ReMi | Dose density of natural killer cells | DOX treatment concentration | Ciliobrevin D treatment concentration |
| --- | --- | --- | --- | --- |
| PBS | — | — | — | — |
| DOX | — | — | 0.3 μM | — |
| DOX + NK | — | 2.4 × 10⁴ cells/well | 0.3 μM | — |
| ReMi | 20 μL | — | 0.3 μM | — |
| NK | — | 2.4 × 10⁴ cells/well | — | — |
| NK + CD | — | 2.4 × 10⁴ cells/well | — | 100 μM |
| ReNK | 20 μL | 2.4 × 10⁴ cells/well | 0.3 μM | — |
| ReNK + CD | 20 μL | 2.4 × 10⁴ cells/well | 0.3 μM | 100 μM |

As illustrated in FIG. 13, it was identified that in a case where Ciliobrevin D (CD) that inhibits formation of lytic granules of the natural killer cells is administered (NK+CD or ReNK+CD), the overall anti-cancer capacity of the natural killer cells was decreased. This well explains necessity of a system in which drug delivery is realized by lytic granules. On the other hand, it was identified that ReNK exhibited anti-cancer capacity corresponding to 70%, which identified that simultaneous delivery of anti-cancer immunotherapy and anti-cancer chemotherapy was effective. It was also identified that in a case where a drug delivery vehicle carrying a drug was administered in a state of being attached to a natural killer cell, it was possible to simultaneously implement drug delivery systems of immunotherapy and chemotherapy, and thus an increased anti-cancer effect was exhibited.

EXAMPLE 5

Identification of Anti-Cancer Effect of Drug Delivery Vehicle through Animal Model Female Balb/c-nu/nu mice were inoculated intravenously with A549-LUC cells at 1×10⁷ cells/mouse. One day later, different samples were injected intravenously for respective experimental groups under the conditions as shown in Table 2. Again, one day later, the cardiac blood was collected from the mice, and IFN-γ levels in plasma were measured by ELISA. The results are illustrated in FIG. 14. Here, ReNK means natural killer cells to which ReMi is attached, and ReMi used was the one carrying 0.3 μM doxorubicin, prepared in Example 1.4. In addition, IFN-γ is an immune cytokine, and higher IFN-γ means higher anti-cancer cytotoxicity.

TABLE 2

| Sample name | Dose density of natural killer cells | DOX treatment concentration |
| --- | --- | --- |
| PBS | — | — |
| DOX | — | 1 mg/kg |
| DOX + NK | 1 × 10⁷ cells | 1 mg/kg |
| NK | 1 × 10⁷ cells | — |
| ReNK | 1 × 10⁷ cells | 0.65 mg/kg |

As illustrated in FIG. 14, it was identified that in a case where ReNK was administered to mice into which cancer cells had been administered, IFN-γ levels were significantly increased, which meant that cytotoxicity of natural killer cells was actively exhibited. In addition, in this in vivo experiment, ReNK exhibited remarkably superior results than NK+DOX, unlike the in vitro experiment of Example 4, and such results are understood as resulting from the fact that the drug delivery vehicle is attached to natural killer cells and the natural killer cells target cancer cells so that the drug is released. Therefore, it was identified that ReMi was attached to natural killer cells so that the natural killer cells were enhanced and thus exhibited a remarkably increased anti-cancer effect.

EXAMPLE 6

Identification of Metastatic Tumorigenicity Inhibitory Effect of Drug Delivery Vehicle through Animal Model Female Balb/c-nu/nu mice were inoculated intravenously with A549-LUC cells at 1×10⁷ cells/mouse. One day later, different samples were injected intravenously for respective experimental groups under the conditions as shown in Table 2, and the mice were raised for cancer growth for three weeks after administration. Subsequently, some mice were intraperitoneally injected with luciferase and then euthanized. The lungs were collected therefrom, and luminescence of A549-LUC was measured through an in vivo imaging system, as illustrated in FIG. 15. The luminescence was quantified, and the results are illustrated in FIG. 16. Some other mice were anesthetized and positron emission tomography (PET) images were obtained therefrom under anesthesia. The results are illustrated in FIG. 17. Subsequently, the mice were euthanized. The lungs were collected therefrom, and then ex vivo positron emission tomography (PET) images were obtained. The results are illustrated in FIG. 18. The images of FIGS. 17 and 18 were quantified, and the results are illustrated in FIG. 19.

As illustrated in FIGS. 15 and 16, it was identified that the ReNK-administered experimental group had remarkably smaller sized cancer than the other experimental groups, which identified that an excellent metastatic tumorigenicity inhibitory effect was exhibited.

In addition, as illustrated in FIGS. 17 to 19, it was identified that the ReNK-administered experimental group also had lower luminescence of cancer cells than the other experimental groups, which identified that the immune cells were enhanced both in vivo and ex vivo to inhibit metastatic tumorigenicity.

From the results of Examples 1 to 6, it was identified that the drug delivery vehicle of the present invention, in a micellar structure, was attached to the surface of natural killer cells and caused the natural killer cells to change into strong immune cells with excellent cancer cell-killing capacity, and it was found that such strong immune cells exhibited an excellent anti-cancer effect.

The invention claimed is:
1. A block copolymer comprising:
  a hydrophilic first block;
  a hydrophobic second block; and
  a functional group capable of specifically binding to thiol,
  wherein the hydrophobic second block includes, in its main chain, a unit that is decomposed at a condition of pH 4.5 to 7, includes, in its main or side chain, a unit that becomes cationic at a condition of pH 4.5 to 7, or includes both units,
  wherein the block copolymer is represented by Formula 5 and includes a functional group capable of specifically binding to thiol:

[Formula 5]

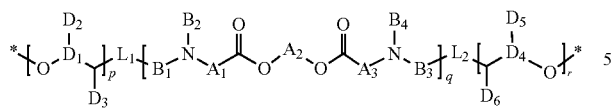

in the formula,
- $A_1$ and $A_3$ are each independently selected from a $C_1$ to $C_5$ linear or branched alkylene group; a $C_2$ to $C_5$ linear or branched alkenylene group; and a $C_2$ to $C_5$ linear or branched alkynylene group,
- $A_2$ is selected from a $C_1$ to $C_{10}$ linear or branched alkylene group; a $C_2$ to $C_{10}$ linear or branched alkenylene group; and a $C_2$ to $C_{10}$ linear or branched alkynylene group,
- $B_1$ and $B_3$ are each independently selected from a $C_1$ to $C_{10}$ linear or branched alkylene group; a $C_2$ to $C_{10}$ linear or branched alkenylene group; and a $C_2$ to $C_{10}$ linear or branched alkynylene group,
- $B_2$ and $B_4$ are each independently selected from hydrogen; a $C_1$ to $C_{10}$ linear or branched alkyl group; a $C_2$ to $C_{10}$ linear or branched alkenyl group; a $C_2$ to $C_{10}$ linear or branched alkynyl group; a $C_1$ to $C_{10}$ linear or branched alkylene group; a $C_2$ to $C_{10}$ linear or branched alkenylene group; and a $C_2$ to $C_{10}$ linear or branched alkynylene group,
- wherein $B_1$ and $B_2$ may be connected to each other to form a $C_3$ to $C_{20}$ alicyclic or aromatic ring, and
- $B_3$ and $B_4$ may be connected to each other to form a $C_3$ to $C_{20}$ alicyclic or aromatic ring,
- $D_1$ and $D_4$ are each independently a $C_1$ or $C_2$ alkylene group,
- $D_2$, $D_3$, $D_5$, and $D_6$ are each independently selected from hydrogen; halogen; a hydroxyl group; and a methyl group,
- $L_1$ and $L_2$ are linkers, and
- p, q, and r are each independently an integer of 1 to 100.

2. The block copolymer of claim 1, wherein the block copolymer has a molecular weight of 1,000 to 50,000 Da.

3. The block copolymer of claim 1, wherein the functional group capable of specifically binding to thiol is contained in an amount of 0.01 to 5% by weight, based on the total weight of the block copolymer.

4. The block copolymer of claim 1, wherein a ratio of the total weight of the hydrophilic first block to the total weight of the hydrophobic second block is (1:20) to (20:1).

5. The block copolymer of claim 1, wherein the functional group capable of specifically binding to thiol is selected from a disulfide group, a maleimide group, an alkenyl group, an alkynyl group, and combinations thereof.

6. The block copolymer of claim 1, wherein the functional group capable of specifically binding to thiol is connected, directly or via a linker, to the block copolymer's main chain, side chain, or end, or a combination thereof.

7. The block copolymer of claim 1, wherein (p+r)/q is (1:10) to (10:1).

8. The block copolymer of claim 1, wherein L1 is represented by Formula 4, and $L_2$ is represented by Formula 6:

[Formula 4]

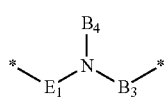

[Formula 6]

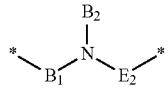

in the formulas,
- $B_1$ and $B_3$ are each independently selected from a $C_1$ to $C_{10}$ linear or branched alkylene group; a $C_2$ to $C_{10}$ linear or branched alkenylene group; and a $C_2$ to $C_{10}$ linear or branched alkynylene group,
- $B_2$ and $B_4$ are each independently selected from hydrogen; halogen; a $C_1$ to $C_{10}$ linear or branched alkyl group; a $C_2$ to $C_{10}$ linear or branched alkenyl group; a $C_2$ to $C_{10}$ linear or branched alkynyl group; a $C_1$ to $C_{10}$ linear or branched alkylene group; a $C_2$ to $C_{10}$ linear or branched alkenylene group; and a $C_2$ to $C_{10}$ linear or branched alkynylene group, and
- $E_1$ and $E_2$ are each independently a unit derived from a functional group capable of reacting with amine,
- wherein $B_1$ and $B_2$ may be connected to each other to form a $C_3$ to $C_{20}$ alicyclic or aromatic ring, and
- $B_3$ and $B_4$ may be connected to each other to form a $C_3$ to $C_{20}$ alicyclic or aromatic ring.

9. The block copolymer of claim 1, wherein the block copolymer is represented by Formula 7:

[Formula 4]

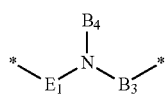

[Formula 6]

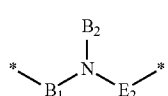

in the formula,
- p and r are each independently an integer of 5 to 100, and
- q is an integer of 1 to 60.

10. A nanoparticle, comprising:
the block copolymer of claim 1.

11. A drug delivery vehicle, comprising:
a nanoparticle comprisirw the block copolymer of claim 1; and
a drug.

12. The drug delivery vehicle of claim 11, wherein the drug is selected from anti-cancer agents, anti-proliferative or chemotherapeutic drugs, analgesic agents, anti-inflammatory agents, antiparasitic agents, antiarrhythmic agents, antibacterial agents, antiviral agents, anticoagulants, antidepressants, antidiabetics, antiepileptic agents, antifungal agents, antigout agents, antihypertensives, antimalarials, antimigraines, anti-muscarinic agents, anti-neoplastic agents, antierectile dysfunction agents, immunosuppressants, antiprotozoals, anti-thyroid agents, anti-anxiety agents, sedatives, hypnotics, neuroleptics, β-blockers, cardiotonic agents, corticosteroids, diuretics, anti-Parkinson's disease agents, gastrointestinal agents, histamine receptor antagonists, keratolytic agents, lipid modulators, angina pectoris drugs, Cox-2 inhibitors, leukotriene inhibitors, macrolides, muscle relaxants, nutrients, narcotic analgesics, protease inhibitors, sex hormones, stimulants, muscle relaxants, anti-osmotic agents, anti-obesity drugs, cognitive enhancers, urinary incontinence drugs, benign prostatic drugs, essential fatty acids, non-essential fatty acids, and combinations thereof.

13. A modified cell, comprising:
    a drug delivery vehicle comprising a nanoparticle, wherein the nanopaiticie includes the block copolymer of claim 1; and
    an immune cell.

14. The modified cell of claim 13, wherein the immune cell is selected from T cells, natural killer cells, dendritic cells (DCs), macrophages, microglial cells, and combinations thereof.

15. An anti-cancer pharmaceutical composition comprising:
    the block copolymer of claim 1; and
    an anti-cancer drug.

16. The anti-cancer pharmaceutical composition of claim 15, wherein the cancer is selected from colon cancer, lung cancer, non-small cell lung cancer, bone cancer, pancreatic cancer, skin cancer, head cancer, cervical cancer, skin melanoma, intraocular melanoma, uterine cancer, ovarian cancer, rectal cancer, gastric cancer, perianal cancer, breast cancer, fallopian tube carcinoma, endometrial carcinoma, cervical carcinoma, vaginal carcinoma, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penis cancer, prostate cancer, chronic leukemia, acute leukemia, lymphocyte lymphoma, bladder cancer, kidney cancer, ureteral cancer, renal cell carcinoma, renal pelvic carcinoma, and central nervous system (CNS) tumor.

17. A method for preventing or treating a cancer or infection in a subject in need thereof, comprising:
    administering to the subject the block copolymer of claim 1, a drug, and an immune cell.

18. The method of claim 17, wherein the cancer is selected from colon cancer, lung cancer, non-small cell lung cancer, bone cancer, pancreatic cancer, skin cancer, head cancer, cervical cancer, skin melanoma, intraocular melanoma, uterine cancer, ovarian cancer, rectal cancer, gastric cancer, perianal cancer, breast cancer, fallopian tube carcinoma, endometrial carcinoma, cervical carcinoma, vaginal carcinoma, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penis cancer, prostate cancer, chronic leukemia, acute leukemia, lymphocyte lymphoma, bladder cancer, kidney cancer, ureteral cancer, renal cell carcinoma, renal pelvic carcinoma, and central nervous system (CNS) tumor.

* * * * *

UNITED STATES PATENT AND TRADEMARK OFFICE
CERTIFICATE OF CORRECTION

PATENT NO. : 12,115,261 B2
APPLICATION NO. : 17/278272
DATED : October 15, 2024
INVENTOR(S) : Kim et al.

Page 1 of 1

It is certified that error appears in the above-identified patent and that said Letters Patent is hereby corrected as shown below:

In the Specification

Column 20, Line 59, "!mop" should be -- µmol) --.

Column 20, Line 65, "!mop" should be -- µmol) --.

Column 20, Line 67, "!mop" should be -- µmol) --.

Column 22, Line 65, "t.tM" should be -- µM --.

In the Claims

Claim 11, Column 26, Line 47, "comprisirw" should be -- comprising --.

Claim 13, Column 27, Line 5, "nanopaiticie" should be -- nanoparticle --.

Signed and Sealed this
Eighteenth Day of February, 2025

Coke Morgan Stewart
*Acting Director of the United States Patent and Trademark Office*